United States Patent
Townsend et al.

(10) Patent No.: US 10,836,844 B2
(45) Date of Patent: Nov. 17, 2020

(54) REDOX POLYMERIZABLE COMPOSITION WITH PHOTOLABILE REDUCING AGENTS

(71) Applicant: 3M INNOVATIVE PROPERTIES COMPANY, St. Paul, MN (US)

(72) Inventors: Erik M. Townsend, Hastings, MN (US); William H. Moser, Edina, MN (US); Shantanu R. Ranade, Woodbury, MN (US); Kathleen S. Shafer, Woodbury, MN (US); Michael A. Kropp, Cottage Grove, MN (US); Ross E. Behling, Woodbury, MN (US); Jason D. Clapper, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 106 days.

(21) Appl. No.: 15/772,173

(22) PCT Filed: Nov. 23, 2016

(86) PCT No.: PCT/US2016/063443
§ 371 (c)(1),
(2) Date: Apr. 30, 2018

(87) PCT Pub. No.: WO2017/095704
PCT Pub. Date: Jun. 8, 2017

(65) Prior Publication Data
US 2018/0312613 A1 Nov. 1, 2018

Related U.S. Application Data

(60) Provisional application No. 62/262,588, filed on Dec. 3, 2015.

(51) Int. Cl.
| | |
|---|---|
| C07D 307/32 | (2006.01) |
| C07D 307/33 | (2006.01) |
| C08F 4/40 | (2006.01) |
| C07D 407/14 | (2006.01) |
| C07D 307/62 | (2006.01) |
| C07D 307/04 | (2006.01) |
| C08F 222/10 | (2006.01) |
| A61K 6/30 | (2020.01) |
| C08F 22/10 | (2006.01) |
| B01J 37/16 | (2006.01) |
| C08J 9/00 | (2006.01) |
| C08K 5/1535 | (2006.01) |
| C09D 4/00 | (2006.01) |
| A61K 6/887 | (2020.01) |
| B01J 37/12 | (2006.01) |
| C08F 20/18 | (2006.01) |

(52) U.S. Cl.
CPC .......... *C08F 4/40* (2013.01); *A61K 6/30* (2020.01); *B01J 37/16* (2013.01); *C07D 307/04* (2013.01); *C07D 307/62* (2013.01); *C07D 407/14* (2013.01); *C08F 22/1006* (2020.02); *C08F 222/1006* (2013.01); *C08J 9/0023* (2013.01); *C08K 5/1535* (2013.01); *A61K 6/887* (2020.01); *B01J 37/12* (2013.01); *C07D 307/32* (2013.01); *C07D 307/33* (2013.01); *C08F 20/18* (2013.01); *C08J 2333/08* (2013.01); *C08J 2333/10* (2013.01); *C09D 4/00* (2013.01)

(58) Field of Classification Search
None
See application file for complete search history.

(56) References Cited

U.S. PATENT DOCUMENTS

| | | |
|---|---|---|
| 2,801,185 A | 7/1957 | Iler |
| 3,330,661 A | 7/1967 | Beavers |
| 3,496,250 A | 2/1970 | Czerwinski |
| 4,503,169 A | 3/1985 | Randklev |
| 4,522,958 A | 6/1985 | Das |
| 5,061,812 A | 10/1991 | Satoh |
| 5,130,347 A | 7/1992 | Mitra |
| 5,154,762 A | 10/1992 | Mitra |
| 5,252,694 A | 10/1993 | Willett |
| 5,721,289 A | 2/1998 | Karim |
| 5,925,715 A | 7/1999 | Mitra |
| 5,962,550 A | 10/1999 | Akahane |
| 6,126,922 A | 10/2000 | Rozzi |
| 6,387,981 B1 | 5/2002 | Zhang |
| 6,572,693 B1 | 6/2003 | Wu |
| 6,586,483 B2 | 7/2003 | Kolb |
| 6,670,436 B2 | 12/2003 | Burgath |
| 6,730,156 B1 | 4/2004 | Windisch |
| 6,794,520 B1 | 9/2004 | Moszner |

(Continued)

FOREIGN PATENT DOCUMENTS

| | | |
|---|---|---|
| CN | 1099753 A | 3/1995 |
| CN | 101541776 A | 9/2009 |

(Continued)

OTHER PUBLICATIONS

Aguirre-Soto "Visible-Light Organic photocatalysis for latent radical-initiated polymerization via 2e/1H transfers: initiation with parallels to photosynthesis", JACS, 2014, vol. 136, No. 20, pp. 7418-7427.
Ciesienski, "A photolabile ligand for light-activated release of caged copper", JACS, 2008, vol. 130, No. 37, pp. 12246-12247.
Ciesienski, "Development of next-generation photolabile copper cages with improved copper binding properties", The royal society of chemistry, 2010, vol. 39, No. 40, pp. 9538-9546.
Dahlgren, "Solid-phase library synthesis of reversed-statine type inhibitors of the, alarial aspartyl preteases plasmepsin I and II", Bioorganic and medicinal chemistry, Mar. 2003,vol. 11, No. 6, pp. 827-841.

(Continued)

*Primary Examiner* — Richard A Huhn

(57) ABSTRACT

Polymerizable compositions comprising a redox initiator system is disclosed. The redox initiators comprises a photolabile reducing agent, that photolyzes and initiates the redox cycle. Dental compositions comprising dental resins and the photolabile redox initiator system are also described.

14 Claims, No Drawings

(56) References Cited

U.S. PATENT DOCUMENTS

| | | |
|---|---|---|
| 7,074,839 B2 | 7/2006 | Fansler |
| 7,090,721 B2 | 8/2006 | Craig |
| 7,090,722 B2 | 8/2006 | Budd |
| 7,156,911 B2 | 1/2007 | Kangas |
| 7,241,437 B2 | 7/2007 | Davidson |
| 7,342,047 B2 | 3/2008 | Lewandowski |
| 7,598,298 B2 | 10/2009 | Lewandowski |
| 7,648,029 B2 | 1/2010 | Chen |
| 7,674,850 B2 | 3/2010 | Karim |
| 7,888,400 B2 | 2/2011 | Abuelyaman |
| 8,440,827 B2 | 5/2013 | Franz |
| 8,551,976 B2 | 10/2013 | Franz |
| 2005/0017966 A1 | 1/2005 | Engl |
| 2005/0065300 A1 | 3/2005 | Lewandowski |
| 2010/0021869 A1 | 1/2010 | Abuelyaman |
| 2011/0041736 A1 | 2/2011 | Gartner |
| 2012/0270962 A1 | 10/2012 | Hecht |
| 2013/0012614 A1 | 1/2013 | Abuelyaman |
| 2013/0210793 A1 | 8/2013 | Franz |
| 2015/0284601 A1 | 10/2015 | Yurt |

FOREIGN PATENT DOCUMENTS

| | | |
|---|---|---|
| CN | 102952503 | 3/2013 |
| EP | 0202589 | 11/1986 |
| EP | 0609899 A1 | 8/1994 |
| EP | 2401998 | 1/2012 |
| EP | 2902387 | 8/2015 |
| WO | WO 2001-030305 | 5/2001 |
| WO | WO 2001-030307 | 5/2001 |
| WO | WO 2003-063804 | 8/2003 |
| WO | WO 2008-082881 | 7/2008 |
| WO | WO 2008/124660 A2 | 10/2008 |
| WO | WO 2012-146914 | 11/2012 |
| WO | WO 2013-055944 | 4/2013 |
| WO | WO 2013-151739 | 10/2013 |
| WO | WO 2014-078115 | 5/2014 |
| WO | WO 2014-093014 | 6/2014 |
| WO | WO 2014-172185 | 10/2014 |
| WO | WO 2016-195970 | 12/2016 |
| WO | WO 2016-196541 | 12/2016 |
| WO | WO 2017-078883 | 5/2017 |
| WO | WO 2017-079189 | 5/2017 |
| WO | WO 2017-095704 | 6/2017 |

OTHER PUBLICATIONS

Fors, "Control of a living radical polymerization of methacrylates by light", Angewandte communications, 2012, vol. 51, No. 35, pp. 8850-8853.

Klan, "Photoremovable protecting groups in chemistry and biology: reaction mechanisms and efficacy", American chemical society, 2012, vol. 113, pp. 119-191.

Kumbhar, "Light uncages a copper complex to induce nonapoptotic cell death", The royal society of chemistry, 2013, vol. 49, No. 24, pp. 2460-2462.

Matyjaszewski, "Atom transfer radical polymerization", Chemical Review, 2001, vol. 101, No. 9, pp. 2921-2990.

Misra, "Redox polymerization", Progress in polymer science,1982, vol. 8, No. 1-2, pp. 61-131.

Pelliccioli, "Photoremovable protecting groups: reaction mechanisms and applications", PPS, 2002, vol. 1, pp. 441-458.

Schachtner. "Organoalane-mediated isomerization of ascorbic and isoascorbic acid derivatives", Tetrahedron: Asymmetry, 1996, vol. 7, No. 11, pp. 3263-3267.

Thopate, "One-pot 2-O-Alkylation of L-ascorbic acid", Synlett, 2013, vol. 24, No. 12, pp. 1555-1557.

Xu, "A robust and versatile photoinduced living polymerization of conjugated and unconjugated monomers and its oxygen tolerance", JACS, 2014, vol. 136, No. 14, pp. 5508-5519.

International Search report for PCT International Application No. PCT/US2016/063443 dated Feb. 6, 2017, 6 pages.

REDOX POLYMERIZABLE COMPOSITION WITH PHOTOLABILE REDUCING AGENTS

CROSS REFERENCE TO RELATED APPLICATIONS

This application is a national stage filing under 35 U.S.C. 371 of PCT/US2016/063443, filed Nov. 23, 2016, which claims the benefit of U.S. Application No. 62/262,588, filed Dec. 3, 2015, the disclosure of which is incorporated by reference in its/their entirety herein.

BACKGROUND

Redox reactions represent an important method for initiating the curing of acrylate, methacrylate and other vinyl-based resin, including adhesive and dental formulations. Redox-initiated curing often has advantages over photoinitiated curing, including improved depth of cure and a slower accumulation of stress during the initial stages of curing.

A significant challenge in the use of redox initiating systems is finding an optimal balance between stability and reactivity. The reactivity of the redox system needs to be sufficiently high for full curing and attainment of mechanical properties within a short period of time. However, if the reactivity is too great, problems such as premature curing, accumulation of stress, and poor shelf stability of the formulation can be encountered.

SUMMARY

Applicants provide a method to overcome these problems by creating an "on demand" redox-initiated cure, in which the reducing agent of the redox cure initiator system has latent activity while the formulation is stored and delivered, but then can be triggered when required.

The present disclosure provides a redox initiator system for initiating polymerization comprising an oxidizing agent, a photolabile reducing agent, and a transition metal complex that participates in a redox cycle. On exposure to actinic radiation, such as UV, the photolabile compound photolyzes, releasing the reducing agent and initiating the redox-initiated polymerization. Advantageously, polymerization of the instant compositions may be initiated by exposure to actinic radiation, but continued irradiation is not required. When the redox initiator system is combined with polymerizable component monomers or oligomers to form a polymerizable composition, the polymerization may be initiated, then build molecular weight and physical properties as the composition continues to cure in the absence of light.

When applied to adhesive compositions, the polymerizable compositions described herein combine the advantages of PSAs and structural adhesives in the form of a one-part photo-triggered PSA-to-(semi)structural acrylic adhesive. This adhesive acts as a conventional PSA in its uncured or partially cured state, offering easy application, high wet-out, and green strength. The application of a short UV-light trigger initiates a radical-producing redox reaction that continues after the light is removed, inducing a steady rate of cure and the concomitant increase in cohesive strength. Finally, the cure will plateau at a level sufficient to give the adhesive structural or semi-structural performance.

This collection of properties and curing behavior would be especially useful in the common case of a permanent bond between two opaque substrates. In the absence of a UV trigger, the modulus of the adhesive lies below the level dictated by the Dahlquist criterion, meaning the material has tack and it can form a bond to a substrate with only the application of pressure. Next, the UV trigger is applied to the exposed face of the tape, initiating the self-sustaining redox reaction but leaving the surface tacky and able to wet out the second substrate within a reasonable period of time ("open time"). After bond closure, the adhesive continues to cure until its modulus reaches a level sufficient for structural strength.

In one aspect, this disclosure provides a polymerizable composition comprising one or more ethylenically-unsaturated polymerizable monomers or oligomers and an initiator system that participates in a reversible redox cycle.

In another aspect, this disclosure provides a dental composition comprising one or more curable dental resins and an initiator system that participates in a reversible redox cycle.

In one aspect, this disclosure provides a structural adhesive composition comprising a multi-functional (meth)acrylate monomer comprising two (preferably three) or more (meth)acrylate groups, and/or a multi-functional (meth)acrylate oligomer and optionally a (meth)acrylate-functional diluent, and an initiator system that participates in a reversible redox cycle.

DETAILED DESCRIPTION

The chemically polymerizable compositions comprise redox initiator systems that include a polymerizable component (e.g., an ethylenically unsaturated polymerizable monomer or oligomer) and a redox initiator system that includes the transition metal complex, an oxidizing agent, and a photolabile reducing agent of the formula:

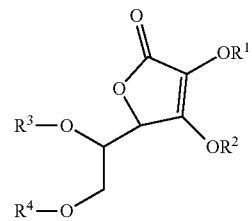

I where
each of $R^1$ and $R^2$ are H, an alkyl, an aryl, or $R^{Photo}$, with the proviso that at least one of $R^1$ and $R^2$ is $R^{Photo}$;
$R^{Photo}$ is a photolabile group;
each of $R^3$ and $R^4$ are independently H, an alkyl, an aryl, having an ester, an ether, a urethane or a carbonate functional group (including the depicted oxygen). For example $R^3$ and $R^4$ may be alkyl-NH—CO—, alkyl-O—, aryl-CO—O—, etc., where the highlighted oxygen is that depicted in Formula I.

In some embodiments $R^3$ and $R^4$ may be taken together to form a five or six member ring, such as by forming a ketal or acetal group. In some preferred embodiments at least one of $R^3$ and $R^4$ comprises a $C_{12}$-$C_{30}$ alkyl chain in an ester, ether, urethane or carbonate group to confer solubility and/or miscibility of the reductant in the polymerizable component mixture.

Any known photolabile group that may be irradiated and which cleaves or fragments to release the transition metal may be used. Reference may be made to Petr Klan et al., Photoremovable Protecting Groups in Chemistry and Biology: Reaction Mechanisms and Efficiency, Chem Reviews, 2013, vol. 113, pp 119-191 and Jacob Wirz et al., Photoremovable Protecting Groups: Reaction Mechanisms and Applications, Photochem. Photobiol. Sci., 2002, Vol. 1, pp. 441-458.

With reference to Formula I, useful photolabile groups "$R^{photo}$" include, but are not limited to, phenacyl groups, 2-alkylphenacyl groups, ethylene-bridged phenacyl groups, o- or p-hydroxyphenacyl groups, benzoin groups, o-nitrobenzyl groups, o-nitro-2-phenethyloxycarbonyl groups, coumarin-4-yl methyl groups, benzyl groups, o-hydroxylbenzyl groups, o-hydroxynapthyl groups, 2,5-dihydroxyl benzyl groups, 9-phenylthioxanthyl, 9-phenylxanthyl groups, anthraquinon-2-yl groups, 8-halo-7-hydroxyquinoline-2-yl methyl groups, and pivaloylglycol groups.

The photolabile compounds of Formula I are generally prepared by alkylating the hydroxyls corresponding to $R^3$ and $R^4$, typically by forming an acetal or ketal, followed by functionalizing at $R^1$ and/or $R^2$ with the photolabile group. As the hydroxy corresponding to $R^2$ is the most acidic, it is preferentially functionalized.

Useful transition metal compounds have the general formula
$[ML_p]^{n+}A^-$, wherein M is a transition metal that participates in a redox cycle,
L is a ligand, A– is an anion, n is the formal charge on the transition metal having a whole number value of 1 to 7, preferably 1 to 3, and p is the number of ligands on the transition metal having a number value of 1 to 9, preferably 1 to 2.

Useful transition metals, M, include the catalytically active valent states of Cu, Fe, Ru, Cr, Mo, Pd, Ni, Pt, Mn, Rh, Re, Co, V, Au, Nb and Ag. Preferred low valent metals include Cu(II), Fe(II), Ru(II) and Co(II). Other valent states of these same metals may be used, and the active low valent state generated in situ.

Useful anions, $A^-$, include halogen, $C_1$-$C_6$ alkoxy, $NO_3^{2-}$, $SO_4^{2-}$, $PO_4^{3-}$, $HPO_4^{2-}$, $PF_6^-$, triflate, hexafluorophosphate, methanesulfonate, arylsulfonate, $CN^-$ and alkyl carboxylates and aryl carboxylates.

The ligand, L, is used to solubilize the transition metal salts in a suitable solvent and adjust the redox potential of the transition metal for appropriate reactivity and selectivity. The ligands can direct the metal complex to undergo the desired one-electron atom transfer process, rather than a two-electron process such as oxidative addition/reductive elimination. The ligands may further enhance the stability of the complexes in the presence of different monomers and solvents or at different temperatures. Acidic monomers and monomers that strongly complex transition metals may still be efficiently polymerized by appropriate selection of ligands.

Useful ligands include those having one or more nitrogen, oxygen, phosphorus and/or sulfur atoms which can coordinate to the transition metal through a σ-bond, ligands containing two or more carbon atoms which can coordinate to the transition metal through a π-bond, and ligands which can coordinate to the transition metal through a μ-bond or an η-bond.

Useful ligands include those having one or more nitrogen, oxygen, phosphorus and/or sulfur atoms which can coordinate to the transition metal through a σ-bond are provided by monodentate and polydentate compounds preferably containing up to about 30 carbon atoms and up to 10 heteroatoms selected from aluminum, boron, nitrogen, sulfur, non-peroxidic oxygen, phosphorus, arsenic, selenium, antimony, and tellurium, where upon addition to the metal atom, following loss of zero, one, or two hydrogens, the polydentate compounds preferably forming with the metal, $M^{n+}$, a 4-, 5-, or 6-membered saturated or unsaturated ring. Examples of suitable monodentate compounds or groups are carbon monoxide, alcohols such as ethanol, butanol, and phenol; pyridine, nitrosonium (i.e., $NO^+$); compounds of Group Vb elements such as ammonia, phosphine, trimethylamine, trimethylphosphine, tributylphosphine, triphenylamine, triphenylphosphine, triphenylarsine, tributylphosphite; nitriles such as acetonitrile, benzonitrile; isonitriles such as phenylisonitrile, butylisonitrile; carbene groups such as ethoxymethylcarbene, dithiomethoxycarbene; alkylidenes such as methylidene and ethylidene.

Suitable polydentate compounds or groups include dipyridyl, 1,2-bis(diphenylphosphino)ethane, 1,2-bis(diphenylarsino)ethane, bis(diphenylphosphino)methane, polyamines such as ethylenediamine, propylenediamine, tetramethyl ethylene diamine, hexamethyl tris-aminoethylamine, diethylenetriamine, 1,3-diisocyanopropane, and hydridotripyrazolylborate; the hydroxycarboxylic acids such as glycolic acid, lactic acid, salicylic acid; polyhydric phenols such as catechol and 2,2'-dihydroxybiphenyl; hydroxyamines such as ethanolamine, propanolamine, and 2-aminophenol; dithiocarbamates such as diethyldithiocarbamate, dibenzyldithiocarbamate; xanthates such as ethyl xanthate, phenyl xanthate; the dithiolenes such as bis(perfluoromethyl)-1,2-dithiolene; aminocarboxylic acids such as alanine, glycine and o-aminobenzoic acid; dicarboxylic diamines as oxalamide, biuret; diketones such as 2,4-pentanedione; hydroxyketones such as 2-hydroxyacetophenone; alpha-hydroxyoximes such as salicylaldoxime; ketoximes such as benzil oxime; 1,10-phenanthroline, porphyrin, cryptands and crown ethers, such as 18-crown-6 and glyoximes such as dimethylglyoxime.

Other suitable ligands that can coordinate to the transition metal through a σ-bond are the inorganic groups such as, for example, $F^-$, $OH^-$, $Cl^-$, $Br^-$, $I^-$, and $H^-$ and the organic groups such as, for example, $CN^-$, $SCN^-$, acetoxy, formyloxy, benzoyloxy, and the like. The ligand can also be a unit of a polymer; for example the amino group in poly(ethyleneamine); the phosphino group in poly(4-vinylphenyldiphenylphosphine); the carboxylic acid group in poly(acrylic acid); and the isonitrile group in poly(4-vinylphenylisonitrile).

Useful ligands containing two or more carbon atoms which can coordinate to the transition metal through a π-bond are provided by any monomeric or polymeric compound having an accessible unsaturated group, i.e., an ethylenic, —C=C— group; acetylenic, —C≡C— group; or aromatic group which has accessible π-electrons regardless of the total molecular weight of the compound.

Illustrative of π-bond ligands are the linear and cyclic ethylenic and acetylenic compounds having less than 100 carbon atoms (when monomeric), preferably having less than 60 carbon atoms, and from zero to 10 heteroatoms selected from nitrogen, sulfur, non-peroxidic oxygen, phosphorous, arsenic, selenium, boron, aluminum, antimony, tellurium, silicon, germanium, and tin, the ligands being those such as ethylene, acetylene, propylene, methylacetylene, α-butene, 2-butene, diacetylene, butadiene, 1,2-dimethylacetylene, cyclobutene, pentene, cyclopentene, hexene, cyclohexene, 1,3-cyclohexadiene, cyclopentadiene, 1,4-cyclohexadiene, cycloheptene, 1-octene, 4-octene, 3,4-dimethyl-3-hexene, and 1-decene; $\eta^3$-allyl, $\eta^3$-pentenyl, norbornadiene, $\eta^5$-cyclohexadienyl, cycloheptatriene, cyclooctatetraene, and substituted and unsubstituted carbocyclic and heterocyclic aromatic ligands having up to 25 rings and up to 100 carbon atoms and up to 10 hetero atoms selected from nitrogen, sulfur, non-peroxidic oxygen, phosphorus, arsenic, selenium, boron, aluminum, antimony, tellurium, silicon, germanium, and tin, such as, for example, $\eta^5$-cyclopentadienyl, benzene, mesitylene, toluene, xylene, tetramethylbenzene, hexamethylbenzene, fluorene, naphthalene, anthracene, chrysene, pyrene, $\eta^7$-cycloheptatrienyl, triphenylmethane, paracyclophane, 1,4-diphenylbutane, $\eta^5$-pyrrole, $\eta^5$-thiophene, $\eta^5$-furan, pyridine, gamma-picoline, quinaldine, benzopyrane, thiochrome, benzoxazine, indole, acridine, carbazole, triphenylene, silabenzene, arsabenzene, stibabenzene, 2,4,6-triphenylphosphabenzene, $\eta^5$-selenophene, dibenzostannepine, $\eta^5$-tellurophene, phenothiazine, selenanthrene, phenoxaphosphine, phenarsazine, phenatellurazine, $\eta^5$-methylcyclopentadienyl, $\eta^5$-pentamethylcyclopentadienyl, and 1-phenylborabenzene. Other suitable aromatic compounds can be found by consulting any of many chemical handbooks.

Preferred ligands include unsubstituted and substituted pyridines and bipyridines, tertiary amines, including polydentate amines such as tetramethyl ethylenediamine and hexamethyl tris-aminoethylamine, acetonitrile, phosphites such as $(CH_3O)_3P$, 1,10-phenanthroline, porphyrin, cryptands and crown ethers, such as 18-crown-6. The most preferred ligands are polydentate amines, bipyridine and phosphites. Useful ligands and ligand-metal complexes useful in the initiator systems of the present invention are described in Matyjaszewski and Xia, *Chem. Rev.*, vol. 101, pp. 2921-2990, 2001.

The molar proportion of photolabile reducing agent (of Formula I) relative to transition metal complex is generally that which is effective to polymerize the selected polymerizable components(s), but may be from 1000:1 to 5:1, preferably from 500:1 to 25:1, more preferably from 250:1 to 50:1, and most preferably from 200:1 to 75:1. The oxidant and photolabile reductant of the redox initiator system are used in approximately equimolar amount. Generally the mole ratio of the oxidant and photolabile reductant is from 1:1.5 to 1.5:1, preferably 1:1.1 to 1.1 to 1.

Suitable oxidizing agents will also be familiar to those skilled in the art, and include but are not limited to persulfuric acid and salts thereof, such as sodium, potassium, ammonium, cesium, and alkyl ammonium salts. Preferred oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, the photolabile reducing agent is present in an amount of at least 0.01 part by weight, and more preferably at least 0.1 parts by weight, based on the total weight of the monomer components of the polymerizable composition. Preferably, the reducing agent is present in an amount of no greater than 10 parts by weight, and more preferably no greater than 5 parts by weight, based on the total weight of the polymerizable components of the polymerizable composition.

Preferably, the oxidizing agent is present in an amount of at least 0.01 part by weight, and more preferably at least 0.10 part by weight, based on the total weight of the polymerizable components of the polymerizable composition. Preferably, the oxidizing agent is present in an amount of no greater than 10 part by weight, and more preferably no greater than 5 parts by weight, based on the total weight of the polymerizable components of the polymerizable composition.

The present disclosure further provides a polymerizable composition comprising the redox initiator system (including transition metal complex, oxidant and photolabile reductant), and at least one polymerizable component monomer, such as vinyl monomers, and (meth)acryloyl monomers (including acrylate esters, amides, and acids to produce (meth)acrylate homo- and copolymers). The redox initiator system is present in the composition in amounts, from about 0.1 to about 10 parts by weight, preferably 0.1 to 5 parts by weight, based on 100 parts by weight of the polymerizable component of the polymerizable composition.

In some embodiments, the polymerizable composition comprises the redox initiator system and one or more vinyl monomers. Vinyl monomers useful in the polymerizable composition include vinyl ethers (e.g. methyl vinyl ether, ethyl vinyl ether), vinyl esters (e.g., vinyl acetate and vinyl propionate), styrene, substituted styrene (e.g., $\alpha$-methyl styrene), vinyl halide, divinylbenzene, alkenes (e.g. propylene, isomers of butylene, pentene, hexylene up to dodecene, isoprene, butadiene) and mixtures thereof.

In some embodiments the polymerizable composition comprises one or more (meth)acrylate ester monomer(s). (Meth)acrylate ester monomer useful in preparing (meth) acrylate (co)polymers are monomeric (meth)acrylic ester of a non-tertiary alcohol, which alcohol contains from 1 to 14 carbon atoms and preferably an average of from 4 to 12 carbon atoms.

Examples of monomers suitable for use as the (meth) acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl-alcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomers are suitable. In some embodiments, the preferred (meth)acrylate ester monomer is the ester of (meth)acrylic acid with an alcohol derived from a renewable source, such as 2-octanol, citronellol, or dihydrocitronellol.

In some embodiments it is desirable for the (meth)acrylic acid ester monomer to include a high $T_g$ monomer. The homopolymers of these high $T_g$ monomers have a $T_g$ of at least 25° C., and preferably at least 50° C. Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of up to 100 parts by weight, preferably 85 to 99.5 parts by weight based on 100 parts total monomer content used to prepare the polymer, exclusive of the amount of multifunctional (meth)acrylates. Preferably (meth)acrylate ester monomer is present in an amount of 90 to 95 parts by weight based on 100 parts total monomer content. When high $T_g$ monomers are included, the copolymer may include up to 50 parts by weight, preferably up to 20 parts by weight of the (meth)acrylate ester monomer component.

The polymerizable composition may comprise an acid functional monomer, where the acid functional group may be an acid per se, such as a carboxylic acid, or a portion may be a salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic or phosphoric acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 0.5 to 15 parts by weight, preferably 1 to 15 parts by weight, most preferably 5 to 10 parts by weight, based on 100 parts by weight total monomer.

The polymerizable composition may comprise a polar monomer. The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; tetrahydrofurfuryl (meth)acrylate, poly(alkoxyalkyl) (meth)acrylates including 2-(2-ethoxyethoxy)ethyl (meth) acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of tetrahydrofurfuryl (meth)acrylate, 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

The polymerizable composition may further comprise a vinyl monomer when preparing acrylic copolymers. When used, vinyl monomers useful in the (meth)acrylate polymer include vinyl esters (e.g., vinyl acetate and vinyl propionate), styrene, substituted styrene (e.g., α-methyl styrene), vinyl halide, divinylbenzene, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer when preparing acrylic copolymers.

A multifunctional (meth)acrylate may be incorporated into the blend of polymerizable monomers. Examples of useful multifunctional (meth)acrylates include, but are not limited to, di(meth)acrylates, tri(meth)acrylates, and tetra (meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth) acrylate is tailored depending upon application of the adhesive composition, for example, adhesives, hardcoats or dental resins.

Typically, the multifunctional (meth)acrylate is present in amounts up to 100 parts, preferably 0.1 to 100 parts, based 100 parts by weight of remaining polymerizable monofunctional monomers. In some embodiments the multifunctional (meth)acrylate is used in amounts of greater than 50 parts by weight, based on the 100 parts by weight of remaining polymerizable monomers. In some embodiments, the multifunctional (meth)acrylate may be present in amounts from 0.01 to 5 parts, preferably 0.05 to 1 parts, based on 100 parts total monomers of the polymerizable composition for adhesive applications, and greater amounts for hardcoats.

In such embodiments, an acrylic copolymer may be prepared from a polymerizable composition comprising:
  i. up to 100 parts by weight, preferably 85 to 99.5 parts by weight of an (meth)acrylic acid ester;
  ii. 0 to 15 parts by weight, preferably 0.5 to 15 parts by weight of an acid functional ethylenically unsaturated monomer;
  iii. 0 to 15 parts by weight of a non-acid functional, ethylenically unsaturated polar monomer;
  iv. 0 to 5 parts by weight vinyl monomer;
  v. 0 to 100 parts by weight of a multifunctional (meth) acrylate, preferably 50 to 100 parts by weight, relative to i-iv;
and
  vi. the redox initiator system (including the complex, oxidant and photolabile reductant) in amounts from about 0.1 weight percent to about 5.0 weight percent, relative to 100 parts total monomer i-v.

The polymerizable composition may also include other additives. Examples of suitable additives include tackifiers (e.g., rosin esters, terpenes, phenols, and aliphatic, aromatic, or mixtures of aliphatic and aromatic synthetic hydrocarbon resins), surfactants, plasticizers (other than physical blowing agents), nucleating agents (e.g., talc, silica, or $TiO_2$), pigments, dyes, reinforcing agents, solid fillers, stabilizers (e.g., UV stabilizers), and combinations thereof. The additives may be added in amounts sufficient to obtain the desired properties for the cured composition being produced. The desired properties are largely dictated by the intended application of the resultant polymeric article.

Adjuvants may optionally be added to the compositions such as colorants, abrasive granules, anti-oxidant stabilizers, thermal degradation stabilizers, light stabilizers, conductive particles, tackifiers, flow agents, film-forming polymers, bodying agents, flatting agents, inert fillers, binders, blowing agents, fungicides, bactericides, surfactants, plasticizers, rubber tougheners and other additives known to those skilled in the art. They also can be substantially unreactive, such as fillers, both inorganic and organic. These adjuvants, if present, are added in an amount effective for their intended purpose.

In some embodiments, a toughening agent may be used. The toughening agents which are useful in the present invention are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski), incorporated herein by reference. Preferable rubbery backbones comprise polymerized butadiene or a polymerized mixture of butadiene and styrene. Preferable shells comprising polymerized methacrylic acid esters are lower alkyl ($C_1$-$C_4$) substituted methacrylates. Preferable monovinyl aromatic hydrocarbons are styrene, alphamethylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would poison the catalyst.

Examples of useful toughening agents of the second type are acrylate core-shell graft copolymers wherein the core or backbone is a polyacrylate polymer having a glass transition temperature below about 0° C., such as polybutyl acrylate or polyisooctyl acrylate to which is grafted a polymethacrylate polymer (shell) having a glass transition above about 25° C., such as polymethylmethacrylate.

The third class of toughening agents useful in the invention comprises elastomeric particles that have a glass transition temperature ($T_g$) below about 25° C. before mixing with the other components of the composition. These elastomeric particles are polymerized from free radical polymerizable monomers and a copolymerizable polymeric stabilizer that is soluble in the resins The free radical polymerizable monomers are ethylenically unsaturated monomers or diisocyanates combined with coreactive difunctional hydrogen compounds such as diols, diamines, and alkanolamines.

Useful toughening agents include core/shell polymers such as methacrylate-butadiene-styrene (MBS) copolymer wherein the core is crosslinked styrene/butadiene rubber and the shell is polymethylacrylate (for example, ACRYLOID KM653 and KM680, available from Rohm and Haas, Philadelphia, Pa.), those having a core comprising polybutadiene and a shell comprising poly(methyl methacrylate) (for example, KANE ACE M511, M521, B11A, B22, B31, and M901 available from Kaneka Corporation, Houston, Tex. and CLEARSTRENGTH C223 available from ATOFINA, Philadelphia, Pa.), those having a polysiloxane core and a polyacrylate shell (for example, CLEARSTRENGTH S-2001 available from ATOFINA and GENIOPERL P22 available from Wacker-Chemie GmbH, Wacker Silicones, Munich, Germany), those having a polyacrylate core and a poly(methyl methacrylate) shell (for example, PARALOID EXL2330 available from Rohm and Haas and STAPHYLOID AC3355 and AC3395 available from Takeda Chemical Company, Osaka, Japan), those having an MBS core and a poly(methyl methacrylate) shell (for example, PARALOID EXL2691A, EXL2691, and EXL2655 available from Rohm and Haas) and the like and mixtures thereof. Preferred modifiers include the above-listed ACRYLOID and PARALOID modifiers and the like, and mixtures thereof.

The toughening agent is useful in an amount equal to about 1-35 parts by weight, preferably about 3-25 parts by weight, relative to 100 parts by weight of the polymerizable component of the polymerizable composition. The toughening agent adds strength to the composition after curing without reacting with the component of the polymerizable composition or interfering with curing.

In some embodiments the polymerizable composition may include one or more non-free radically polymerizable film-forming polymer. The term "film-forming organic polymer" refers to an organic polymer that will uniformly coalesce upon drying. Film-forming polymers suitable for use in the compositions are generally thermoplastic organic polymers.

Examples of suitable polymers include: polyesters, for example, polyethylene terephthalate or polycaprolactone; copolyesters, for example, polyethylene terephthalate isophthalate; polyamides, for example, polyhexamethylene adipamide; vinyl polymers, for example, poly(vinyl acetate/methyl acrylate), poly(vinylidene chloride/vinyl acetate); polyolefins, for example, polystyrene and copolymers of styrene with acrylate(s) such as, for example, poly(styrene-co-butyl acrylate); polydienes, for example, poly(butadiene/styrene); acrylic polymers, for example, poly(methyl methacrylate-co-ethyl acrylate), poly(methyl acrylate-co-acrylic acid); polyurethanes, for example, reaction products of aliphatic, cycloaliphatic or aromatic diisocyanates with polyester glycols or polyether glycols; and cellulosic derivatives, for example, cellulose ethers such as ethyl cellulose and cellulose esters such as cellulose acetate/butyrate. Combinations of film-forming polymers may also be used. Methods and materials for preparing aqueous emulsions or latexes of such polymers are well known, and many are widely available from commercial sources.

In some embodiments the crosslinkable composition may include filler. In some embodiments the total amount of filler is at most 50 wt. %, preferably at most 30 wt. %, and more preferably at most 10 wt. % filler. Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

In some embodiments the filler may be surface modified. A variety of conventional methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference.

Surface-modifying groups may be derived from surface-modifying agents. Schematically, surface-modifying agents can be represented by the formula X—Y, where the X group is capable of attaching to the surface of the particle (i.e., the silanol groups of a silica particle) and the Y group is a reactive or non-reactive functional group. A non-functional group does not react with other components in the system (e.g. the substrate). Non-reactive functional groups can be selected to render the particle relatively more polar, relatively less polar or relatively non-polar. In some embodiments the non-reactive functional group "Y" is a hydrophilic group such as an acid group (including carboxylate, sulfonate and phosphonate groups), ammonium group or poly(oxyethylene) group, or hydroxyl group. In other embodiments, "Y" may be a reactive functional group such as an ethylenically unsaturated polymerizable group, including vinyl, allyl, vinyloxy, allyloxy, and (meth)acryloyl, that may be free-radically polymerized with the polymerizable resin or monomers.

Such optional surface-modifying agents may be used in amounts such that 0 to 100%, generally 1 to 90% (if present) of the surface functional groups (Si—OH groups) of the silica nanoparticles are functionalized. The number of functional groups is experimentally determined where quantities of nanoparticles are reacted with an excess of surface modifying agent so that all available reactive sites are functionalized with a surface modifying agent. Lower percentages of functionalization may then be calculated from the result. Generally, the amount of surface modifying agent is used in amount sufficient to provide up to twice the equal weight of surface modifying agent relative to the weight of inorganic nanoparticles. When used, the weight ratio of surface modifying agent to inorganic nanoparticles is preferably 2:1 to 1:10. If surface-modified silica nanoparticles are desired, it is preferred to modify the nanoparticles prior to incorporation into the coating composition.

The present polymerizable compositions are also useful in the preparation of hardcoats and structural or semi-structural adhesives. The term "hardcoat" or "hardcoat layer" means a layer or coating that is located on the external surface of an object, where the layer or coating has been designed to at least protect the object from abrasion.

The present disclosure provides hardcoat compositions comprising the redox initiator system and a multifunctional (meth)acrylate monomer comprising two (preferably three) or more (meth)acrylate groups, and/or a multifunctional (meth)acrylate oligomer and optionally a (meth)acrylate-functional diluent.

Useful multifunctional (meth)acrylate monomers comprise three or more (meth)acrylate groups. Multifunctional (meth)acrylate monomers are useful in the practice of the present invention because they add abrasion resistance to the hard coat layer. Preferred multifunctional (meth)acrylate monomers comprising three or more (meth)acrylate groups include trimethylol propane tri(meth)acrylate (TMPTA), and pentaerythritol tri(meth)acrylate, pentaerythritol tetra(meth)acrylate, dipentaerithritol tri(meth)acrylate (Sartomer 355), dipentaerythritol penta(meth)acrylate (Sartomer 399), dipentaerythritol hydroxy penta(meth)acrylate (DPHPA), glyceryl propoxy tri(meth)acrylate, trimethylolpropane tri(meth)acrylate, and mixtures thereof. Another useful radiation-curable component of the present invention is the class of multifunctional (meth)acrylate oligomers, having two or more (meth)acrylate groups, and having an average molecular weight ($M_w$) in the range from about 400 to 2000.

Useful multifunctional (meth)acrylate oligomers include polyester (meth)acrylates, polyurethane (meth)acrylates, and (meth)acrylated epoxy (meth)acrylates. (Meth)acrylated epoxy (meth)acrylates and polyester(meth)acrylates are most preferred because they tend to have a relatively low viscosity and therefore allow a more uniform layer to be applied by the spin coating method. Specifically, preferred multifunctional (meth)acrylate oligomers include those commercially available from UCB Radcure, Inc. of Smyrna, Ga. and sold under the trade name Ebecryl (Eb): Eb40 (tetrafunctional acrylated polyester oligomer), ENO (polyester tetra-functional (meth)acrylate oligomer), Eb81 (multifunctional (meth)acrylated polyester oligomer), Eb600 (bisphenol A epoxy di(meth)acrylate), Eb605 (bisphenol A epoxy di(meth)acrylate diluted with 25% tripropylene glycol di(meth)acrylate), Eb639 (novolac polyester oligomer), Eb2047 (trifunctional acrylated polyester oligomer), Eb3500 (di-functional Bisphenol-A oligomer acrylate), Eb3604 (multi-functional polyester oligomer acrylate), Eb6602 (trifunctional aromatic urethane acrylate oligomer), Eb8301 (hexafunctional aliphatic urethane acrylate), EbW2 (difunctional aliphatic urethane acrylate oligomer), and mixtures thereof. Of these, the most preferred are, Eb 600, Eb605, Eb80, and Eb81.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art.

In some embodiments, the multifunctional (meth)acrylate oligomers may comprise a reactive oligomer having pendent polymerizable groups comprising:
a) greater than 50 parts by weight, preferably greater than 75 parts by weight, most preferably greater than 80 parts by weight of (meth)acrylate ester monomer units;
b) 1 to 10 parts by weight, preferably 1 to 5 parts by weight, most preferably 1 to 3 parts by weight, of monomer units having a pendent, free-radically polymerizable functional group,
c) 0 to 20 parts by weight of other polar monomer units, wherein the sum of the monomer units is 100 parts by weight.

The reactive oligomer may be represented by the formula:

$$-[M^{Unsatd}]_o[M^{ester}]_p[M^{polar}]_q-, \qquad \text{II}$$

where
$[M^{Unsatd}]$ represents monomer units having a pendent, free-radically polymerizable functional groups and subscript "o" is the parts be weight thereof;
$[M^{ester}]$ represents (meth)acrylate ester monomer units and subscript "p" represents the parts by weight thereof; and
$[M^{polar}]$ represents polar monomer units and subscript "q" represents the parts by weight thereof.

The reactive oligomers (II) of the composition comprise one or more pendent groups that include free-radically polymerizable unsaturation, including (meth)acryloyl, (meth)acryloxy, propargyl, vinyl, allyl, acetylenyl and (meth)acrylamide. That is, the monomer units $[M^{Unsatd}]$ contain such polymerizable groups.

An indirect method of incorporating pendent polymerizable unsaturated groups into the oligomers is to include a reactive functional group among the monomer units of the precursor oligomer that may be further functionalized with an ethylenically unsaturated compound having a functional groups that is co-reactive with the functional group of the precursor oligomer.

Useful reactive functional groups include, but are not limited to, hydroxyl, amino, oxazolonyl, oxazolinyl, acetoacetyl, azlactonyl, carboxyl, isocyanato, epoxy, aziridinyl, acyl halide, and cyclic anhydride groups. Preferred among these are carboxyl, hydroxyl, amino, azlactonyl and aziridinyl groups. These pendent reactive functional groups are reacted with unsaturated compounds that comprise functional groups that are co-reactive with the reactive pendent functional group. When the two functional groups react, an oligomer with pendent unsaturation results. In some applications, it may be desirable to use less than a stoichiometric equivalent of unsaturated compounds that comprise co-reactive functional groups, so that some of the pendent functional groups on the oligomer(s) remain unreacted. Specifically, the reactive oligomers of Formula II may be prepared from a precursor oligomer having monomer units of the formula [M$^{FG}$], having reactive functional groups that may be functionalized to provide the reactive oligomer of Formula II.

Using the "indirect method" of incorporating the pendent, free-radically polymerizable functional groups, useful reactive functional groups include hydroxyl, secondary amino, oxazolinyl, oxazolonyl, acetyl, acetonyl, carboxyl, isocyanato, epoxy, aziridinyl, acyl halide, vinyloxy, and cyclic anhydride groups. Where the pendent reactive functional group is an isocyanato functional group, the co-reactive functional group preferably comprises a secondary amino or hydroxyl group. Where the pendent reactive functional group comprises a hydroxyl group, the co-reactive functional group preferably comprises a carboxyl, ester, acyl halide, isocyanato, epoxy, anhydride, azlactonyl or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophile and electrophilic functional groups.

Preferred ethylenically unsaturated compounds that may be used to functionalize the precursor oligomer have the general formula:

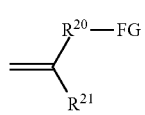

IV wherein R$^{21}$ is hydrogen, a C$_1$ to C$_4$ alkyl group, or a phenyl group, preferably hydrogen or a methyl group; R$^{20}$ is a single bond or a divalent linking group that joins an ethylenically unsaturated group to a co-reactive functional group "FG" and preferably contains up to 34, preferably up to 18, more preferably up to 10, carbon and, optionally, oxygen and nitrogen atoms and, when R$^{20}$ is not a single bond, is preferably selected from

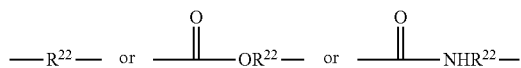

in which R$^{22}$ is an alkylene group having 1 to 6 carbon atoms, a 5- or 6-membered cycloalkylene group having 5 to 10 carbon atoms, or an alkylene-oxyalkylene in which each alkylene includes 1 to 6 carbon atoms or is a divalent aromatic group having 6 to 16 carbon atoms; and FG is a co-reactive functional group, that is capable of reacting with a pendent reactive functional group of the oligomer for the incorporation of a free-radically polymerizable functional group.

Representative examples of useful compounds of Formula IV having co-reactive functional groups include hydroxyalkyl (meth)acrylates such as 2-hydroxyethyl (meth)acrylate, 3-hydroxypropyl (meth)acrylate, 2, 3-dihydroxypropyl (meth)acrylate, 4-hydroxybutyl (meth)acrylate and 2-(2-hydroxyethoxy)ethyl (meth)acrylate; aminoalkyl (meth)acrylates such as 3-aminopropyl (meth)acrylate and 4-aminostyrene; oxazolinyl compounds such as 2-ethenyl-1,3-oxazolin-5-one, 2-vinyl-4,4-dimethyl-1,3-oxazolin-5-one, 2-isopropenyl-4,4-dimethyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl (meth)acrylate; epoxy-substituted compounds such as glycidyl (meth)acrylate; aziridinyl-substituted compounds such as N-acryloylaziridine and 1-(2-propenyl)-aziridine; and acryloyl halides such as (meth) acryloyl chloride.

The reactive oligomer may be redox polymerized per se, or with a multifunctional acrylate, such as hexanediol di(meth)acrylate. The reactive oligomer having pendent polymerizable groups may be prepared as described in U.S. Pat. No. 7,598,298 (Lewandowski et al.), U.S. Pat. No. 7,342,047 (Lewandowski et al.) and U.S. Pat. No. 7,074,839 (Fansler et al.), each incorporated herein by reference.

The polymerizable reactive oligomer component may further comprise a diluent monomer. The (meth)acrylate-functional diluents, also referred to herein as "reactive diluents", are relatively low molecular weight mono- or di-functional, non-aromatic, (meth)acrylate monomers. These relatively low molecular weight reactive diluents are advantageously of a relatively low viscosity, e.g., less than about 30 centipoise (cps) at 25° C. Di-functional, non-aromatic (meth)acrylates are generally preferred over mono-functional non-aromatic (meth)acrylates because di-functional non-aromatic (meth)acrylates allow for quicker cure time. Preferred reactive diluents include 1,6-hexanediol di(meth)acrylate (HDDA from UCB Radcure, Inc. of Smyrna, Ga.), tripropylene glycol di(meth)acrylate, isobornyl (meth)acrylate (1130A, Radcure), 2(2-ethoxyethoxy) ethyl (meth)acrylate (sold under the trade name Sartomer 256 from SARTOMER Company, Inc. of Exton, Pa.), n-vinyl formamide (Sartomer 497), tetrahydrofurfuryl (meth) acrylate (Sartomer 285), polyethylene glycol di(meth)acrylate (Sartomer 344), tripropylene glycol di(meth)acrylate (Radcure), neopentyl glycol dialkoxy di(meth)acrylate, polyethyleneglycol di(meth)acrylate, and mixtures thereof.

In some embodiments the polymerizable composition may comprise:
20-80 parts by weight of multifunctional (meth)acrylate monomers and/or multifunctional (meth)acrylate reactive oligomers,
0 to parts by weight range of (meth)acrylate diluent,
20 to 75 wt. % of silica (per se, whether or not functionalized), and
from about 0.1 weight percent to about 5.0 weight percent of the redox initiator system, based on the 100 parts by weight of the polymerizable components of the polymerizable composition.

In some embodiments, the polymerizable composition provides a structural and semi-structural adhesive composition in which the partially cured composition may be disposed between two substrates (or adherends), and subsequently fully cured to effect a structural or semi-structural bond between the substrates. "Semi-structural adhesives" are those cured adhesives that have an overlap shear strength of at least about 0.5 MPa, more preferably at least about 1.0 MPa, and most preferably at least about 1.5 MPa. Those cured adhesives having particularly high overlap shear strength, however, are referred to as structural adhesives. "Structural adhesives" are those cured adhesives that have an overlap shear strength of at least about 3.5 MPa, more preferably at least about 5 MPa, and most preferably at least about 7 MPa.

In some embodiments the present disclosure provides an adhesive composition comprising the redox initiator system and a) a first reactive oligomer comprising (meth)acrylate ester monomer units, hydroxyl-functional monomer units, and monomer units having polymerizable groups; b) a second component comprising $C_2$-$C_4$ alkylene oxide repeat units and polymerizable terminal groups, and c) a diluent monomer component.

The first component reactive oligomer is of the general formula:

where
-[$M^{Ester}$]- represents interpolymerized (meth)acrylate ester monomer units and subscript a is greater than 50 parts by weight;
-[$M^{OH}$]- represents interpolymerized (meth)acryloyl monomer units having a pendent hydroxy groups where subscript b represents 0 to 20 parts by weight,
[$M^{Polar}$] represent optional polar monomer units, where subscript c is 0-20, preferably 1-10 parts by weight,
[$M^{Silyl}$] represent silyl functional monomer units, where subscript e is 0 to 10, preferably 1-5 parts by weight; and
[$M^{Poly}$] represents monomer units comprising polymerizable groups silane-functional monomer units and subscript d represents 1-10 parts by weight. The sum of subscripts a to e being 100 parts by weight. Such reactive oligomers are further described in Applicant's copending US 2015/0284601 (Yurt et al., incorporated herein by reference) and in WO 2014/078115 (Behling et al.). As taught in Yurt '601, the oligomer is functionalized with the polymerizable groups ($M^{Poly}$ units) by functionalization of the pendent hydroxy groups of the $M^{OH}$ monomer. The a second component of the Yurt '601 composition is at comprising $C_2$-$C_4$ alkylene oxide units and 1 to 3 terminal polymerizable groups, such as (meth)acrylate groups.

In some embodiments the amount of silica, including the silica modified with conventional surface modifying agents and unmodified silica is 20-75 wt. %, preferably 50-70 wt. %.

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

The present polymerization may be conducted in bulk, or in a solvent. Solvents, preferably organic, can be used to assist in the dissolution of the initiator and initiator system in the polymerizable monomers, and as a processing aid. Preferably, such solvents are not reactive with components. It may be advantageous to prepare a concentrated solution of the transition metal complex in a small amount of solvent to simplify the preparation of the polymerizable composition.

Suitable solvents include ethers such as diethyl ether, ethyl propyl ether, dipropyl ether, methyl t-butyl ether, di-t-butyl ether, glyme (dimethoxyethane), diglyme, diethylene glycol dimethyl ether; cyclic ethers such as tetrahydrofuran and dioxane; alkanes; cycloalkanes; aromatic hydrocarbon solvents such as benzene, toluene, o-xylene, m-xylene, p-xylene; halogenated hydrocarbon solvents; acetonitrile; lactones such as butyrolactone, and valerolactones; ketones such as acetone, methyl ethyl ketone, methyl isobutyl ketone, cyclopentanone, and cyclohexanone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl) ethanol, and 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, Methyl Cellosolve™ and methyl formate; and other solvents such as methylene chloride, nitromethane, acetonitrile, glycol sulfite and 1,2-dimethoxyethane (glyme), mixtures of such solvents, and supercritical solvents (such as $CO_2$). The present polymerization may also be conducted in accordance with known suspension, emulsion and precipitation polymerization processes.

Preferably, the monomer(s) and components of the redox initiator system are selected such that the rate of initiation is not less than 1,000 times (preferably not less than 100 times) slower than the rate of propagation and/or transfer of the generated radical group to the polymer radical. In the present application, "propagation" refers to the reaction of a polymer radical with a monomer to form a polymer-monomer adduct radicals.

Polymerizing may be conducted at a temperature of from −78 to 200° C., preferably from 0 to 160° C. and most preferably from 20 to 100° C. The reaction should be conducted for a length of time sufficient to convert at least 10% (preferably at least 50%, more preferably at least 75% and most preferably at least 90%) of the monomer to polymer. Typically, the reaction time will be from several minutes to 5 days, preferably from 30 minutes to 3 days, and most preferably from 1 to 24 hours.

Preferably the polymerizable composition comprises a "two-part" system in which the transition metal complex is in the first mixture, and the oxidizing agent, the photolabile reducing agent and any filler is in a second mixture. The polymerizable monomer may be part of the first and/or second mixture and is preferably in the first mixture. The two parts are combined, optionally coated on a substrate, and the redox reaction initiated by exposure to actinic radiation. In another embodiment, the polymerizable composition comprises a "two-part" system in which the transition metal complex, photolabile reducing agent and polymerizable monomer component is in the first mixture, and the oxidant is in the second mixture.

The polymerizable composition and the redox initiator system may be combined and irradiated with activating UV radiation to cleave or fragment the photolabile transition metal complex, initiate the redox cycle and polymerize the polymerizable component(s). UV light sources can be of two types: 1) relatively low light intensity sources such as backlights which provide generally 10 mW/cm² or less (as measured in accordance with procedures approved by the United States National Institute of Standards and Technology as, for example, with a Uvimap™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm², preferably between 15 and 450 mW/cm². Where actinic radiation is used to fully or partially polymerize the polymerizable composition, high intensities and short exposure times are preferred. For example, an intensity of 600 mW/cm² and an exposure time of about 1 second may be used successfully. Intensities can range from about 0.1 to about 150 mW/cm², preferably from about 0.5 to about 100 mW/cm², and more preferably from about 0.5 to about 50 mW/cm². UV LEDs may also be used, such as a Clearstone UV LED lamp (Clearstone Technologies Inc., Hopkins, Minn. 385 nm).

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating, knife coating, and die coating. These various methods of coating allow the compositions to be placed on the substrate at variable thicknesses thus allowing a wider range of use of the compositions.

The polymerizable compositions may be coated upon a variety of flexible and inflexible substrates using conventional coating techniques to produce coated articles. Flexible substrates are defined herein as any material which is conventionally utilized as a tape backing or may be of any other flexible material. Examples include, but are not limited to, plastic films such as polypropylene, polyethylene, polyvinyl chloride, polyester (polyethylene terephthalate), polycarbonate, polymethyl(meth)acrylate (PMMA), cellulose acetate, cellulose triacetate, and ethyl cellulose. Foam backings may be used.

In some preferred embodiments, the substrate may be chosen so as to be transparent to the UV radiation used to initiate the redox cycle. The coated article may then be initiated through the thickness of the transparent substrate.

In some embodiments, the substrate is a release liner to form an adhesive article of the construction substrate/adhesive layer/release liner or release liner/adhesive/release liner. The adhesive layer may be cured, uncured or partially cured. Release liners typically have low affinity for the curable composition. Exemplary release liners can be prepared from paper (e.g., Kraft paper) or other types of polymeric material. Some release liners are coated with an outer layer of a release agent such as a silicone-containing material or a fluorocarbon-containing material. Release coating can be applied by solvent or solvent-free methods The present disclosure further provides curable dental compositions comprising the redox initiator system. Although various curable dental compositions have been described, industry would find advantage in compositions having improved properties such as improved working time, and reduced stress deflection and/or reduced shrinkage while maintaining sufficient mechanical properties and depth of cure.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein:

"dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"curable" is descriptive of a material or composition that can be polymerized or crosslinked by a free-radical means such as by irradiating with actinic irradiation to induce polymerization and/or crosslinking; "hardened" refers to a material or composition that has been cured (e.g., polymerized or crosslinked).

"initiator" refers to something that initiates curing of a resin. An initiator may include, for example, a polymerization initiator system, a photoinitiator system, a thermal initiator and/or a redox initiator system.

"self-etching" composition refers to a composition that bonds to a dental structure surface without pretreating the dental structure surface with an etchant. Preferably, a self-etching composition can also function as a self-primer wherein no separate etchant or primer are used.

a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

a "dental structure surface" refers to tooth structures (e.g., enamel, dentin, and cementum) and bone.

an "uncut" dental structure surface refers to a dental structure surface that has not been prepared by cutting, grinding, drilling, etc.

an "untreated" dental structure surface refers to a tooth or bone surface that has not been treated with an etchant, primer, or bonding agent prior to application of a self-etching adhesive or a self-adhesive composition of the present invention.

an "unetched" dental structure surface refers to a tooth or bone surface that has not been treated with an etchant prior to application of a self-etching adhesive or a self-adhesive composition of the present invention.

The total amount of the redox initiator system in the polymerizable resin portion of the unfilled curable dental composition is typically no greater than 5 wt. %. Generally, the amount of redox initiator system is from about 0.1 to 5 wt. % of the polymerizable portion of the unfilled dental composition.

The curable dental compositions comprise at least one ethylenically unsaturated resin monomer or oligomer in combination with the redox initiator system. In some embodiments, such as primers, the ethylenically unsaturated monomer may be monofunctional, having a single (e.g. terminal) ethylenically unsaturated group. In other embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

The amount of curable resin in the dental composition is a function of the desired end use (adhesives, cements, restoratives, etc.) and can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

In favored embodiments, such ethylenically unsaturated groups of the curable dental resin includes (meth)acryloyl such as (meth)acrylamide and (meth)acrylate. Other ethylenically unsaturated polymerizable groups include vinyl and vinyl ethers. The ethylenically unsaturated terminal polymerizable group(s) is preferably a (meth)acrylate group, particularly for compositions that are hardened by exposure to actinic (e.g. UV and visible) radiation in the presence of the redox initiator system. Further, methacrylate functionality is typically preferred over the acrylate functionality in curable dental compositions. The ethylenically unsaturated monomer may comprise various ethylenically unsaturated monomers, as known in the art, for use in dental compositions.

In favored embodiments, the dental composition comprises one or more dental resins having a low volume shrinkage monomer. Preferred (e.g. filled) curable dental compositions (useful for restorations such as fillings and crowns) comprise one or more low volume shrinkage resins such that the composition exhibits a Watts Shrinkage of less than about 2%, preferably no greater than 1.80%, more preferably no greater than 1.60%. In favored embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

Preferred low volume shrinkage monomers include isocyanurate resins, such as described in U.S.S.N. 2013/0012614 (Abuelyaman et al.); tricyclodecane resins, such as described in U.S.S.N 2011/041736 (Eckert et al.); polymerizable resins having at least one cyclic allylic sulfide moiety such as described in U.S. Pat. No. 7,888,400 (Abuelyaman et al.); methylene dithiepane silane resins as described in U.S. Pat. No. 6,794,520 (Moszner et al.); and di-, tri, and/or tetra-(meth)acryloyl-containing resins such as described in U.S. 2010/021869 (Abuelyaman et al.); each of which are incorporated herein by reference.

In favored embodiments, the majority of the unfilled polymerizable resin composition comprises one or more low volume shrinkage monomers ("Low shrinkage monomers"). For example, at least 50%, 60%, 70%, 80%, 90% or more of the unfilled polymerizable resin may comprise low volume shrinkage monomer(s).

In one embodiment, the dental composition comprises at least one isocyanurate resin. The isocyanurate resin comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated free radically polymerizable groups are generally bonded to the core or backbone unit via a (e.g. divalent) linking group.

The trivalent isocyanurate core structure generally has the formula:

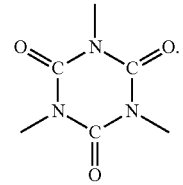

The divalent linking group comprises at least one nitrogen, oxygen or sulfur atom. Such nitrogen, oxygen or sulfur atom forms a urethane, ester, thioester, ether, or thioether linkage. Ether and especially ester linkages can be beneficial over isocyanurate resin comprising urethane linkages for providing improved properties such as reduced shrinkage, and/or increased mechanical properties, e.g., diametral tensile strength (DTS). Thus, in some embodiments, the divalent linking groups of the isocyanurate resin are free of urethane linkages. In some favored embodiments, the divalent linking group comprises an ester linkage such as an aliphatic or aromatic diester linkage.

The isocyanurate monomer typically has the general structure:

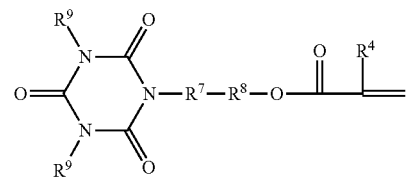

wherein $R^7$ is a (hetero)hydrocarbyl group including straight chain, branched or cyclic alkylene, arylene, or alkarylene, and optionally including a heteroatom (e.g. oxygen, nitrogen, or sulfur); $R^4$ is hydrogen or C1-C4 alkyl; $R^8$ is heterohydrocarbyl group including alkylene, arylene, or alkarylene linking group comprising at least one moiety selected from urethane, ester, thioester, ether, or thioether, and combinations of such moieties; and at least one of the $R^9$ groups is

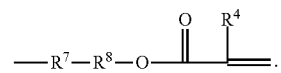

$R^7$ is typically a straight chain, branched or cyclic alkylene, optionally including a heteroatom, having no greater than 12 carbons atoms. In some favored embodiments, $R^7$ has no greater than 8, 6, or 4 carbon atoms. In some favored embodiments, $R_7$ comprises at least one hydroxyl moiety.

In some embodiments, $R^8$ comprises an aliphatic or aromatic ester linkage such as a diester linkage.

In some embodiments, $R^8$ further comprises one or more ether moieties. Hence, the linking group may comprise a combination of ester or diester moieties and one or more ether moieties.

For embodiments, wherein the isocyanurate monomer is a di(meth)acrylate monomer, $R^9$ is hydrogen, alkyl, aryl, or alkaryl, optionally including a heteroatom.

The polymerizable resin portion of the curable unfilled dental composition described herein may comprise at least 10 wt. %, 15 wt. %, 20 wt. %, or 25 wt. %, multifunctional ethylenically unsaturated isocyanurate resin(s). The isocyanurate resin may comprise a single monomer or a blend of two or more isocyanurate resins. The total amount of isocyanurate resin(s) in the unfilled polymerizable resin portion of the curable dental composition is typically no greater than 90 wt. %, 85 wt. %, 80 wt. %, or 75 wt. %.

The filled curable dental composition described herein typically comprises at least 5 wt. %, 6 wt. %, 7 wt. %, 8 wt. %, or 9 wt. % of multifunctional ethylenically unsaturated isocyanurate resin(s). The total amount of isocyanurate resin(s) of the filled hardenable (i.e. polymerizable) dental composition is typically no greater than 20 wt. %, or 19 wt. %, or 18 wt. %, or 17 wt. %, or 16 wt. %, or 15 wt. %.

In another embodiment, the dental composition comprises at least one tricyclodecane resin. The tricyclodecane resin may comprise a single monomer or a blend of two or more tricyclodecane resins. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

Tricyclodecane monomers generally have the core structure (i.e. backbone unit (U):

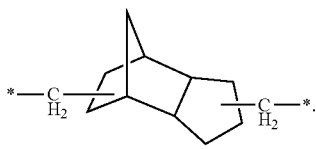

The backbone unit (U) if the tricyclodecane resin typically comprises one or two spacer unit(s) (S) bonded to the backbone unit (U) via an ether linkage. At least one spacer unit (S) comprises a $CH(R^{10})$—OG chain, wherein each group G comprises a (meth)acrylate moiety and $R^{10}$ comprises at least one group selected from hydrogen, alkyl, aryl, alkaryl and combinations thereof. In some embodiments, $R^{10}$ is hydrogen, methyl, phenyl, phenoxymethyl, and combinations thereof. G may be bonded to the spacer unit(s) (S) via a urethane moiety.

In some embodiments, the spacer unit(s) (S) typically comprise

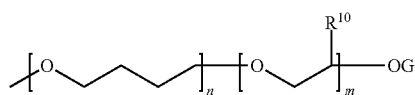

wherein m is 1 to 3; n is 1 to 3; and $R^{10}$ is hydrogen, methyl, phenyl, phenoxymethyl.

In other embodiments, the spacer unit(s) (S) typically comprise

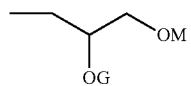

wherein M=aryl.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

In some embodiments, the curable dental composition comprises a polymerizable resin having at least one cyclic allylic sulfide moiety with at least one (meth)acryloyl moiety.

The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth)acrylate moiety) or a (meth)acryloylamino (i.e., a (meth)acrylamide moiety).

In one embodiment, the low shrinkage resin includes those represented by the formulae:

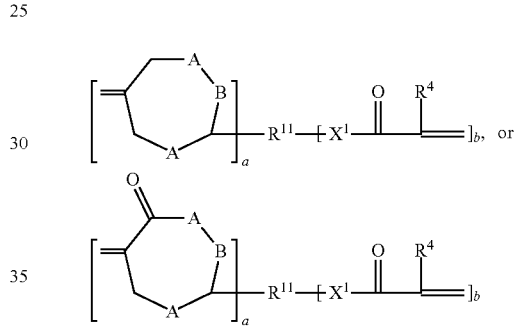

In the above formulae, each A can be independently selected from S, O, N, C (e.g., $C(R^{10})_2$, where each $R^{10}$ is independently a H or an organic group), SO, $SO_2$, N-alkyl, N-acyl, NH, N-aryl, carboxyl or carbonyl group, provided that at least one X is S or a group comprising S. Preferably, each A is sulfur.

B is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with B thus being either absent or methylene, respectively. In some embodiments, B is either absent or is a C1 to C3 alkylene, optionally including a heteroatom, carbonyl, acyl, or combinations thereof.

$X^1$ is independently —O— or —$NR^4$—, where $R^4$ is H or $C_1$-$C_4$ alkyl.

The $R^{11}$ group represents a linker selected from alkylene (typically having more than one carbon atom, i.e. excluding methylene), alkylene optionally including a heteroatom (e.g., O, N, S, S—S, SO, $SO_2$), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

$R^4$ is H or $C_1$-$C_4$ alkyl, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

The inclusion of a polymerizable compound having at least one cyclic allylic sulfide moiety can result in a synergistic combination of low volume shrinkage in combination with high diametral tensile strength.

In another embodiment, the dental composition comprises a low shrinkage resin that includes at least one di-, tri-, and/or tetra (meth)acryloyl-containing resins having the general formula:

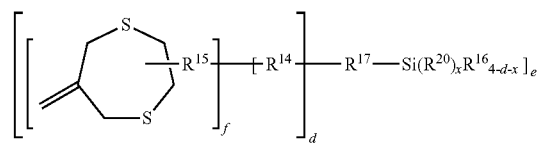

in which $R^{14}$ is a saturated or unsaturated aliphatic or alicyclic hydrocarbon radical with 1 to 10 carbon atoms, which can be interrupted by one or more oxygen and/or sulfur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^{15}$ has one of the meanings given for $R^{14}$ or is absent; $R^{16}$ has one of the meanings given for $R^{14}$ or is absent; $R^{17}$ is equal to —$(CHR^{19})_n$—, —W—CO—NH—$(CHR^{19})_n$—, —Y—CO—NH—$R^{18}$—, —$(CHR^{19})_n$, —$SR^{18}$—, —CO—O—$R^{18}$— or is absent, with n being equal to 1 to 4, $R^{19}$ is hydrogen, $C_1$ to $C_{10}$ alkyl or $C_6$ to $C_{10}$ aryl, $R^{18}$ has one of the meanings given for $R^{14}$ and W stands for an O or S atom or is absent; with $R^{18}$ and $R^{19}$ being able to be substituted or unsubstituted; $R^{20}$ is a hydrolyzable group; d, e, f and x each independently of each other being 1, 2 or 3; and the sum of d+x=2 to 4.

The multifunctional low shrinkage resins are (e.g. highly) viscous liquids at about 25° C., yet are flowable. The viscosity as can be measured with a Haake RotoVisco RV1

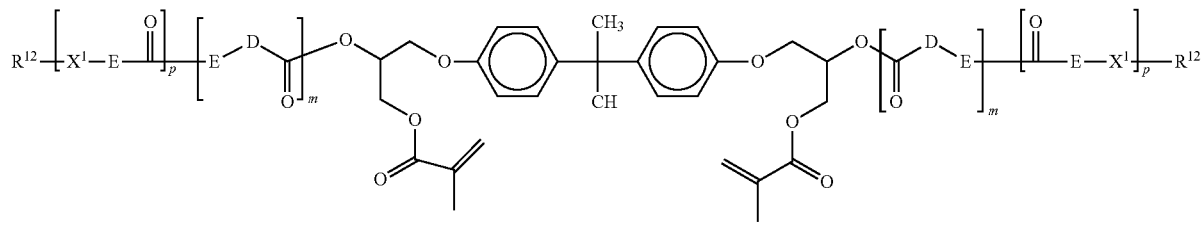

wherein: each $X^1$ is independently —O— or —$NR^4$—, where $R^4$ is H or $C_1$-$C_4$ alkyl;

D and E each independently represent an organic group, and $R^{12}$ represents —C(O)C(CH$_3$)=CH$_2$, and/or p=0 and $R^{12}$ represents H, —C(O)CH=CH$_2$, or —C(O)C(CH$_3$)=CH$_2$, with the proviso that at least one $R^{12}$ is a (meth)acrylate; each m is 1 to 5; p and q are independently 0 or 1. Although this material is a derivative of bisphenol A, when other low volume shrinkage monomer are employed, such as the isocyanurate and/or tricyclodecane monomer, the dental composition is free of (meth)acrylate monomers derived from bisphenol A. Such resins are described in WO 2008/082881 (Abuelyaman et al.)

In another embodiment, the low shrinkage dental resin may be selected from methylene dithiepane silane resins described in U.S. Pat. No. 6,794,520 (Moszner et al.), incorporated herein by reference. Such resins have the general formula device, as described in EP Application No. 10168240.9, filed Jul. 2, 2010 is typically at least 300, or 400, or 500 Pa*s and no greater than 10,000 Pascal-seconds (Pa*s). In some embodiments, the viscosity is no greater than 5000 or 2500 Pa*s.

The ethylenically unsaturated resins of the dental composition are typically stable liquids at about 25° C. meaning that the resins do not substantially polymerize, crystallize, or otherwise solidify when stored at room temperature (about 25° C.) for a typical shelf life of at least 30, 60, or 90 days. The viscosity of the resins typically does not change (e.g. increase) by more than 10% of the initial viscosity.

Particularly for dental restoration compositions, the ethylenically unsaturated resins generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight resin lacking such substituents).

In some embodiments, the (unfilled) polymerizable resin may comprise solely one or more low shrink resins in combination with the redox initiator system. In other embodiments, the (unfilled) polymerizable resin comprises a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt. %, 19 wt. %, 18 wt. %, 17 wt. %, 16 wt. %, or 15 wt. % of the (unfilled) polymerizable resin portion. The concentration of such other monomers is typically no greater than 5 wt. %, 4 wt. %, 3 wt. %, or 2 wt. % of the filled polymerizable dental composition.

In some embodiments, the "other monomers" of the dental composition comprise a low viscosity reactive (i.e. polymerizable) diluent. Reactive diluents typically have a viscosity of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent comprises one or two spacer unit(s) (S) being connected to the backbone unit (U) via an ether linkage; such as described in U.S. 2011/041736 (Eckert et al.); incorporated herein by reference.

The curable component of the curable dental composition can include a wide variety of "other" ethylenically unsaturated compounds (with or without acid functionality), epoxy-functional (meth)acrylate resins, vinyl ethers, and the like.

The polymerizable dental compositions may include free radically polymerizable monomers, agents, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups as an example of an "other monomer". Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are available from a wide variety of commercial sources, such as Sigma-Aldrich, St. Louis.

The curable dental compositions can include at least 1 wt. %, at least 3 wt. %, or at least 5 wt. % ethylenically unsaturated compounds with hydroxyl functionality, based on the total weight of the unfilled composition. The compositions can include at most 80 wt. %, at most 70 wt. %, or at most 60 wt. % ethylenically unsaturated compounds with hydroxyl functionality.

The dental compositions described herein may include one or more curable components in the form of ethylenically unsaturated compounds with acid functionality as an example of an "other" monomer. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. Such acid-functional "other" monomers contribute to the self-adhesion or self-etching of the dental compositions as described in U.S. 2005/017966 (Falsafi et al.), incorporated herein by reference.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components. Also, monomers, oligomers, and polymers of unsaturated carbonic acids such as (meth)acrylic acids, itaconic acid, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C$_1$-C$_4$ hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C$_5$-C$_{12}$ hydrocarbon group; an ethylenically unsaturated compound without acid functionality; an initiator system; and a filler.

The curable dental compositions can include at least 1 wt. %, at least 3 wt. %, or at least 5 wt. % ethylenically unsaturated compounds with acid functionality, based on the total weight of the unfilled composition. The compositions can include at most 80 wt. %, at most 70 wt. %, or at most 60 wt. % ethylenically unsaturated compounds with acid functionality.

The curable dental compositions may include resin-modified glass ionomer cements such as those described in U.S. Pat. No. 5,130,347 (Mitra), U.S. Pat. No. 5,154,762 (Mitra), U.S. Pat. No. 5,925,715 (Mitra et al.) and U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are contemplated.

The chemically hardenable compositions include the redox cure systems that include a polymerizable component (e.g., an ethylenically unsaturated polymerizable component) and redox agents that include an oxidizing agent, the photolabile reducing agent and the transition metal complex.

The photolabile reducing agent, the transition metal complex, and the oxidizing agents react with or otherwise cooperate with one another to produce free-radicals capable of initiating polymerization of the resin system (the ethylenically unsaturated component). Once initiated, this type of cure is not dependent on the continued irradiation and can proceed in the absence of light. The reducing and oxidizing agents are preferably sufficiently shelf-stable and free of undesirable colorization to permit their storage and use under typical conditions.

The reducing agent of the redox initiator system is a photolabile reducing agent of the formula:

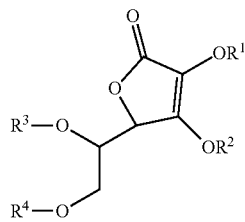

where
each of R$^1$ and R$^2$ are H, an alkyl, an aryl, or R$^{Photo}$, with the proviso that at least one of R$^1$ and R$^2$ is R$^{Photo}$
R$^{Photo}$ is a photolabile group;
each of R$^3$ and R$^4$ are independently H, an alkyl, an aryl, having an ester, an ether, a urethane or a carbonate functional group (including the depicted oxygen).

In some preferred embodiments at least one of R$^3$ and R$^4$ is a C$_{12}$-C$_{30}$ ether, ester, urethane or carbonate group to confer solubility and/or miscibility of the reductant in the polymerizable component mixture Any known photolabile group that may be irradiated and which cleaves or fragments to release the transition metal may be used. Reference may be made to Petr Klan et al., Photoremovable Protecting Groups in Chemistry and Biology: Reaction Mechanisms and Efficiency, Chem Reviews, 2013, vol. 113, pp 119-191 and Jacob Wirz et al., Photoremovable Protecting Groups: Reaction Mechanisms and Applications, Photochem. Photobiol. Sci., 2002, Vol. 1, pp. 441-458.

With reference to Formula I, useful photolabile groups "R$^{photo}$" include, but are not limited to, phenacyl groups, 2-alkylphenacyl groups, ethylene-bridged phenacyl groups, p-hydroxyphenacyl groups, benzoin groups, o-nitrobenzyl groups, o-nitro-2-phenethyloxycarbonyl groups, coumarin-4-yl methyl groups, benzyl groups, o-hydroxylbenzyl groups, o-hydroxynapthyl groups, 2,5-dihydroxyl benzyl groups, 9-phenylthioxanthyl, 9-phenylxanthyl groups, anthraquinon-2-yl groups, 8-halo-7-hydroxyquinoline-2-yl methyl groups, pivaloylglycol groups.

Suitable oxidizing agents will also be familiar to those skilled in the art, and include but are not limited to persulfuric acid and salts thereof, such as sodium, potassium, ammonium, cesium, and alkyl ammonium salts. Preferred oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. The transition metal complex is as is described supra.

The photopolymerizable compositions are typically prepared by admixing the various components of the compositions. For embodiments wherein the polymerizable compositions are not cured in the presence of air, the initiator system is combined under "safe light" conditions (i.e., conditions that do not cause premature hardening of the composition). Suitable inert solvents may be employed if desired when preparing the mixture.

Curing is effected by exposing the composition to a radiation source, preferably a UV light source. It is convenient to employ light sources that emit actinic radiation light between 250 nm and 800 nm (particularly blue light of a wavelength of 320-400 nm) such as quartz halogen lamps, tungsten-halogen lamps, mercury arcs, carbon arcs, low-, medium-, and high-pressure mercury lamps, plasma arcs, light emitting diodes, UV LEDs and lasers. In general, useful light sources have intensities in the range of 500-1500 mW/cm$^2$. A variety of conventional lights for hardening such compositions can be used.

The exposure may be accomplished in several ways. Although the polymerizable composition may be continuously exposed to radiation throughout the entire hardening process (e.g., about 2 seconds to about 60 seconds), the instant initiator system allows one to expose the composition to a single dose of radiation, and then remove the radiation source, thereby allowing polymerization to occur.

In favored embodiments, such as when the dental composition is employed as a dental restorative (e.g. dental filling or crown) or an orthodontic cement, the dental composition typically comprises appreciable amounts of (e.g. nanoparticle) filler. The amount of such fillers is a function of the end use as further described herein. Such compositions preferably include at least 40 wt. %, more preferably at least 45 wt. %, and most preferably at least 50 wt. % filler, based on the total weight of the composition. In some embodiments the total amount of filler is at most 90 wt. %, preferably at most 80 wt. %, and more preferably at most 75 wt. % filler.

The filled dental composite materials typically exhibit a diametral tensile strength (DTS) of at least about 70, 75, or 80 MPa and/or a Barcol Hardness of at least about 60, or 65, or 70. The ISO 4049 depth of cure ranges from about 4 to about 5 mm and is comparable to commercially available (e.g. filled) dental compositions suitable for restorations.

Dental compositions suitable for use as dental adhesives can optionally also include filler in an amount of at least 1 wt. %, 2 wt. %, 3 wt. %, 4 wt. %, or 5 wt. % based on the total weight of the composition. For such embodiments, the total concentration of filler is at most 40 wt. %, preferably at most 20 wt. %, and more preferably at most 15 wt. % filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Suitable inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. Nos. 7,156,911; and 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprises a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 75 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1041, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO™ 1042 or 2327.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The primary particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like and may comprise silane, zirconate or titanate coupling agents. Preferred coupling agents include gamma-methacryloxypropyltrimethoxysilane, gamma-mercaptopropyltriethoxysilane, gamma-aminopropyltrimethoxysilane, and the like.

Suitable copolymerizable or reactive organometallic compounds may have the general formulas: $CH_2=C(R^{22})-R^{21}Si(OR)_nR_{3-n}$ or $CH_2=C(R^{22})-C=OOR^{21}Si(OR)_nR_{3-n}$; wherein R is an $C_1$-$C_4$ alkyl, $R^{21}$ is a divalent organic heterohydrocarbyl linking group, preferably alkylene; $R^{22}$ is H or C1-C4 alkyl; and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, the disclosure provides a universal restorative composite comprising:
a) 15-30 wt. % of a curable dental resin comprising at least two polymerizable, ethylenically unsaturated groups;
b) 70-85 wt. % of an inorganic filler, preferably a surface modified filler;
c) 0.1 to 5 wt. % of the redox initiator system, relative to 100 parts by weight a).

In some embodiments, the disclosure provides a flowable restorative (flowable) composite comprising:

a) 25-50 wt. % of a curable dental resin comprising at least two polymerizable, ethylenically unsaturated groups;
b) 30-75 wt. % of an inorganic filler, preferably a surface modified filler;
c) 0.1 to 5 wt. % of the redox initiator system, relative to 100 parts by weight of a), said curable composition further comprising an initiator and <2% stabilizers, pigments, etc.

In some embodiments, the disclosure provides a resin modified glass-ionomer adhesive comprising:
a) 10-25 wt. % of a partially (meth)acrylated poly(meth) acrylic acid, which includes acrylic acids such as itaconic acid;
b) 5-20 wt. % of a hydroxyalkyl (meth)acrylate;
c) 30-60 wt. % of fluoroaluminosilicate (FAS) acid reactive glass
d) 0-20 wt. % non-acid reactive fillers, preferably surface-treated;
e) 10-20 wt. % water; and
f) 0.1 to 5 wt. % of the redox initiator system, relative to 100 parts by weight of a)-c)
said curable composition further comprising an initiator and <2% stabilizers, or pigments.

Preferably the fluoroaluminosilicate is a silane methacrylate surface-treated fluoroaluminosilicate.

In some embodiments, the disclosure provides a dental adhesive comprising:
a) 30-80 wt. % mono (meth)acrylate monomers;
b) 1-10 wt. % polyfunctional (meth)acrylate monomers;
c) 5-60 wt. % monomers having a acid-functional group (including phosphate, phosphonate, carboxylate, sulfonic acids)
d) 0-10, preferably 1-10 wt. % poly(meth)acrylic acid methacrylate monomers;
e) 0.1 to 5 wt. % of the redox initiator system, relative to 100 parts by weight of a) to d)
f) 0-30 wt. % inorganic filler, preferably surface modified, relative to 100 parts by weight of a) to d);
g) 0 to 25 wt. % solvent relative to 100 parts by weight of a) to d);
h) 0 to 25 wt. % water relative to 100 parts by weight of a) to d); and <2% stabilizers, pigments.

In some embodiments, the dental compositions can have an initial color different than the cured dental structures. Color can be imparted to the composition through the use of a photobleachable or thermochromic dye. As used herein, "photobleachable" refers to loss of color upon exposure to actinic radiation. The composition can include at least 0.001 wt. % photobleachable or thermochromic dye, and typically at least 0.002 wt. % photobleachable or thermochromic dye, based on the total weight of the composition. The composition typically includes at most 1 wt. % photobleachable or thermochromic dye, and more typically at most 0.1 wt. % photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin Bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be cured into dental articles prior to applying. For example, a dental article such as a crown may be pre-formed from the curable dental composition described herein. Dental composite (e.g. crowns) articles can be made from the curable composition described herein by casting the curable composition in contact with a mold and curing the composition. Alternatively, dental composites or articles (e.g. crowns) can be made by first curing the composition forming a mill blank and then mechanically milling the composition into the desired article.

Another method of treating a tooth surface comprises providing a dental composition as described herein wherein the composition is in the form of a (partially cured) curable, self-supporting, malleable structure having a first semi-finished shape; placing the curable dental composition on a tooth surface in the mouth of a subject; customizing the shape of the curable dental composition; and hardening the curable dental composition. The customization can occur in the patient's mouth or on a model outside the patient mouth such as described in U.S. Pat. No. 7,674,850 (Karim et al.); incorporated herein by reference.

EXAMPLES

Unless otherwise indicated, all amounts and percentages are by weight.
Materials Utilized:
Acetone (EMD Millipore Corporation, Billerica, Mass.)
Acm: Acrylamide (Zibo Xinye Chemical Company, Zibo, China)
Ammonium Chloride (EMD Chemicals, Inc. Gibbstown, N.J.)
L-Ascorbic acid (Alfa Aesar, Ward Hill, Mass.)
L-Ascorbic acid-6-palmitate (Alfa Aesar, Ward Hill, Mass.)
BA: n-Butyl acrylate (BASF Corporation, Florham Park, N.J.)
BAYMOD 35.42 (Lanxess, Cologne, Germany)
BDGMA: Butyl diglycol methacrylate (Evonik Industries, Marl, Germany)
BENZOFLEX 9-88, plasticizer (Eastman Chemical Co., Kingsport, Tenn.)
Benzyltributyl ammonium chloride (Sigma-Aldrich, St. Louis, Mo.)
BisGMA: 2,2-Bis[4-hydroxy-3-methacryloyloxy)propoxyphenyl]propane (Sigma-Aldrich, St. Louis, Mo.)
4-Bromomethyl-6,7-dimethoxycoumarin (Sigma-Aldrich, St. Louis, Mo.)
CAB-O-SIL TS720 (Cabot Corporation, Billerica, Mass.)
$CDCl_3$: Deuterochloroform (Cambridge Isotope Laboratories, Andover, Mass.)
$CH_2Cl_2$: Dichloromethane (EMD Millipore Corporation, Billerica, Mass.)
CHA: Cyclohexyl acrylate (TCI America, Portland, Oreg.)
CHMA: Cyclohexyl methacrylate (Evonik Industries, Marl, Germany)
CHP: Cumene hydroperoxide, 80% Tech. grade (Alfa Aesar, Heysham, England)
Cu(naph)2: Copper (II) naphthenate in mineral spirits (8% Cu) (Strem Chemicals, Newburyport, Mass.)
$Cu(OAc)_2$: Copper (II) acetate (Sigma-Aldrich, St. Louis, Mo.)
CSA: 10-Camphorsulfonic acid (Aldrich Chemical Co., Milwaukee, Wis.)
1,1-Dimethoxycyclohexane (Sigma-Aldrich, St. Louis, Mo.)
4,5-Dimethoxy-2-nitrobenzyl alcohol (Sigma-Aldrich, St. Louis, Mo.)
2,2-Dimethoxypropane (Sigma-Aldrich, St. Louis, Mo.)
DMF: Dimethylformamide (EMD Millipore Corporation, Billerica, Mass.)
DMSO: Dimethylsulfoxide (Alfa Aesar, Ward Hill, Mass.)
$d_6$-DMSO: Dimethylsulfoxide-d (Cambridge Isotope Laboratories, Andover, Mass.)
DRAGONITE SW (Applied Minerals, New York, N.Y.)

2EHA: 2-Ethylhexyl acrylate (BASF Corporation, Florham Park, N.J.)
ESS50F (MiniFibers, Inc. Johnson City, Tenn.)
Ethyl-4-chloroacetoacetate (Sigma-Aldrich, St. Louis, Mo.)
EtOAc: Ethyl acetate (VWR International, Radnor, Pa.)
EtOH: Ethanol (EMD Chemicals, Gibbstown, N.J.)
HCl: 1N aq. Hydrochloric acid (VWR, West Chester, Pa.)
HDDA: Hexanediol diacrylate, Sartomer SR238B (Warrington, Pa.)
HDK H18 (Wacker Chemical Corp., Adrian, Mich.)
HDK H-2000 Hydrophobic pyrogenic silica (Wacker Silicones. Wacker Chemical Corp., Adrian, Mich.)
HEMA: 2-Hydroxyethyl methacrylate (Sigma-Aldrich, St. Louis, Mo.)
Hexane (EMD Millipore Corporation, Billerica, Mass.)
HPA: Hydroxypropyl acrylate (BASF Corporation, Florham Park, N.J.)
IEM: 2-Isocyanatoethyl methacrylate (TCI America, Portland, Oreg.)
Isopropanol (EMD Millipore Corporation, Billerica, Mass.)
$K_2CO_3$: Potassium carbonate (Sigma-Aldrich, St. Louis, Mo.)
KRATON 1192 (Kraton, Houston, Tex.)
MEK: Methyl ethyl ketone (J. T. Baker, Center Valley, Pa.)
MeOH: Methanol (EMD Millipore Corporation, Billerica, Mass.)
Methanesulfonic acid (Aldrich Chemical Co., Milwaukee, Wis.)
3-Methoxyphenol (Sigma-Aldrich, St. Louis, Mo.)
$MgSO_4$: Magnesium sulfate, anhydrous (EMD Chemicals, Inc. Gibbstown, N.J.)
NaCl: Sodium chloride (EMD Chemicals, Inc. Gibbstown, N.J.)
$NaHCO_3$: Sodium bicarbonate (EMD Chemicals, Inc. Gibbstown, N.J.)
$Na_2SO_4$: Sodium sulfate (Sigma-Aldrich, St. Louis, Mo.)
2-Nitrobenzyl bromide (Alfa Aesar, Ward Hill, Mass.)
Phosphorous tribromide (Sigma-Aldrich, St. Louis, Mo.)
Potassium iodide (Sigma-Aldrich, St. Louis, Mo.)
Propylene carbonate (Huntsman Chemical Corporation, Salt Lake City, Utah)
SARTOMER SR203: Tetrahydrofuryl methacrylate (Sartomer, Warrington, Pa.)
SARTOMER SR348: Ethoxylated bisphenol A dimethacrylate (Sartomer, Warrington, Pa.)
SARTOMER SR350: Trimethylol propane trimethacrylate (Sartomer, Warrington, Pa.)
SARTOMER SR541: Ethoxylated(6) Bisphenol A dimethacrylate (Sartomer, Warrington, Pa.)
SIPOMER PAM200 (Solvay, Brussels, Belgium)
$SiO_2$: Standard Grade silica gel (230×400 mesh) (Sorbtech, Norcross, Ga.)
T-10 Release liner: silicone-coated release liner (3M, St. Paul, Minn.)
TDDM: Tertiary dodecyl mercaptan (Sartomer, Exton, Pa.)
TEGDMA: Tetraethylene glycol dimethacrylate (TCI America, Portland, Oreg.)
THF: Tetrahydrofuran (Alfa Aesar, Ward Hill, Mass.)
Toluene (EMD Millipore Corp., Billerica, Mass.)
Triethylamine (EMD Chemicals Inc., Gibbstown, N.J.)
VAZO 52: 2,2'-azobis(2,4-dimethylpentatenitrile) (DuPont, Wilmington, Del.)
VTBN: 1300×33 VTBNX (Emerald Performance Materials, Akron, Ohio); methacrylate-functional butadiene-acrylonitrile liquid rubber
Z250: FILTEK Z250 S/T Universal Restorative (3M ESPE)

Test Methods
Determination of Molecular Weight Distribution

The molecular weight distribution of the compounds was characterized using conventional gel permeation chromatography (GPC). The GPC instrumentation, which was obtained from Waters Corporation (Milford, Mass., USA), included a high pressure liquid chromatography pump (Model 1515HPLC), an auto-sampler (Model 717), a UV detector (Model 2487), and a refractive index detector (Model 2410). The chromatograph was equipped with two 5 micrometer PLgel MIXED-D columns, available from Varian Inc. (Palo Alto, Calif., USA).

Samples of polymeric solutions were prepared by dissolving polymer or dried polymer materials in tetrahydrofuran at a concentration of 0.5 percent (weight/volume) and filtering through a 0.2 micrometer polytetrafluoroethylene filter that was available from VWR International (West Chester, Pa., USA). The resulting samples were injected into the GPC and eluted at a rate of 1 milliliter per minute through the columns maintained at 35° C. The system was calibrated with polystyrene standards using a linear least squares fit analysis to establish a calibration curve. The weight average molecular weight ("$M_w$") and the polydispersity index (weight average molecular weight divided by number average molecular weight) were calculated for each sample against this standard calibration curve.

Static Shear Test Method

A selected adhesive material (in MEK solution) was coated onto a T-10 release liner and dried for 30 minutes in a solvent oven at 70° C. A tape sample was made by transferring the resulting film (~5 mil (~127 micrometers)) from the T-10 release liner onto a primed PET backing such that there was a 1"×1" (2.5 cm×2.5 cm) square of adhesive on the end of a strip of backing that measured 1"×~4" (2.5 cm×~10.2 cm). A 2"×3"×0.049" (5.1 cm×7.6 cm×0.12 cm) steel substrate was prepared by washing with toluene and isopropanol. The square of adhesive was applied to the steel substrate to form a bond with the non-coated backing strip hanging below. In some cases, the adhesive was exposed (through the backing) to UVA from a microwave source (total exposure varies by individual experiment, D-bulb, Heraeus Noblelight America, Gaithersburg, Md.). The bonds were rolled with a 10-lb (4.5 kg) static roller and allowed to sit at room temperature for 18 hours. A 1-kg weight was hung from the strip and the time to bond failure was recorded.

Overlap Shear Test Method Sample Preparation

A selected adhesive material (in EtOAc/MEK solution) was coated onto a T-10 release liner and dried for 30 minutes in a solvent oven at 70° C. 1"×4"×0.064" (2.5 cm×10.2 cm×0.16 cm) aluminum substrates were prepared by scrubbing the terminal 1" (2.54 cm) with SCOTCH-BRITE GENERAL PURPOSE HAND PAD #7447 (3M) followed by washing with isopropanol and air-drying. A ½"×1" (1.3 cm×2.5 cm) portion of the adhesive composition was applied to the scrubbed end of one substrate. The release liner was removed and the composition was exposed to UVA from a microwave source (total exposure varies by individual experiment, D-bulb, Heraeus Noblelight America, Gaithersburg, Md.). A second substrate was applied to the irradiated sample, thus closing the bond (bond area ½"×1" (1.3 cm×2.5 cm)). The assembly was wet out by means of applying a static 10-lb (4.5 kg) roller 3 times horizontally and vertically. The bond was clamped with large binder clips and allowed to sit at room temperature for 18-24 hours prior to testing.

Dynamic Overlap Shear Test

A dynamic overlap shear test was performed at ambient temperature using an MTS SINTECH TENSILE TESTER. Test specimens were loaded into the grips and the crosshead was operated at 0.1" (0.25 cm) per minute, loading the specimen to failure. Stress at break was recorded in units of psi, and converted to pascals (or kilopascals).

Cure Monitoring by FTIR

Small disks (~12 mm in diameter, ~0.5 mm thick) of adhesive material were punched out between two release liners. The release liners were removed and the disks placed between two glass microscope slides: setup consists of a top slide (1"×3" (2.5 cm×7.6 cm), pre-cleaned, VWR 48300-025)+silicone rubber gasket (32 mil, 1"×3" (2.5 cm×7.6 cm))+bottom slide (2"×3" (5.1 cm×7.6 cm), pre-cleaned, VWR 48382-179), attached with small binder clip (at top) and mini binder clip (at bottom). The gasket had a square in the middle cut out to allow room for the disk of adhesive to expand laterally as it was compressed between the slides. Initial spectra were taken on a Nicolet IR iS50 spectrometer (Nicolet Thermo Fisher Scientific Inc., Waltham, Mass.). Spectra at various times after or during irradiation were taken as well. The degree of cure was judged by the disappearance of the methacrylate peak between 6221-6100 cm$^{-1}$.

PREPARATIVE EXAMPLES

Preparative Example 1 (PE-1): Synthesis of 5,6-O-isopropylidene-L-ascorbic Acid (p-AA)

This material was prepared according to literature precedence (Bioorg. Med. Chem. 2003, vol. 11, 827). To a suspension of L-ascorbic acid (20.0 g, 114 mmol) in acetone (200 mL) was added 2,2-dimethoxypropane (20.4 g, 196 mmol) and 10-camphorsulfonic acid (1.32 g, 5.68 mmol). The resultant mixture was allowed to stir overnight at room temperature. To the resultant slurry was added approximately 0.6 g triethylamine. A portion of hexane was added to the mixture, and the white precipitate was collected via vacuum filtration, washing with additional hexane. The material was dried under vacuum to afford the desired product (21.0 g, 86% yield). $^1$H NMR was consistent with the desired product.

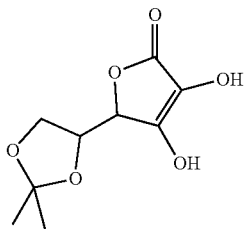

Preparative Example 2 (PE-2): Synthesis of Nitrobenzyl-Protected p-AA

Potassium carbonate (3.03 g, 21.9 mmol) was added to a solution of p-AA (4.73 g, 21.9 mmol) in 40 ml of 1:1 THF/DMSO. The resultant mixture was allowed to stir for 30 min. A solution of 2-nitrobenzyl bromide (4.73 g, 21.9 mmol) in 20 mL of 1:1 THF/DMSO was then added dropwise via addition funnel over 10 min. The resultant mixture was allowed to stir under nitrogen atmosphere overnight, during which time it became dark orange in color. Following removal of the THF under reduced pressure, approximately 200 mL of H$_2$O was added to the mixture, which was then extracted with EtOAc (3×). The combined organic layers were washed with H$_2$O (3×) and sat. aq. NaCl, dried over MgSO$_4$, filtered, and concentrated to an yellow solid. This material was purified via trituration with 2:1 hexane/EtOAc to afford 4.47 g of product as a pale yellow solid (58% yield). $^1$H NMR was consistent with the desired product.

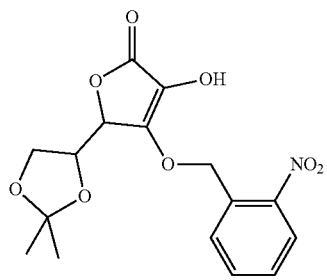 [SMILES: CC1(C)OCC(C2OC(=O)C(O)=C2OCc2ccccc2[N+](=O)[O-])O1]

Preparative Example 3 (PE-3): Synthesis of Nitrobenzyl-Protected Ascorbic Acid The p-AA (4.40 g, 12.5 mmol) was dissolved in 80 mL of 1:1 THF/1N aq. HCl, and the resultant mixture was allowed to stir at room temperature overnight. The THF was removed under reduced pressure, and the remaining aqueous layer was extracted with EtOAc (3×). The combined organic layers were then washed with sat. aq. NaCl, dried over MgSO$_4$, filtered, and concentrated to afford a tan solid. This material was purified via trituration with 1:1 hexane/EtOAc to provide 3.03 g product as a white solid (78% yield). $^1$H NMR was consistent with the desired product.

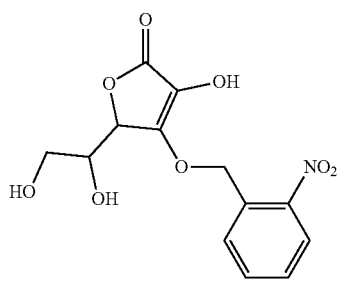 [SMILES: O=C1OC(C(O)CO)C(OCc2ccccc2[N+](=O)[O-])=C1O]

Preparative Example 4 (PE-4): Synthesis of 5,6-O-cyclohexylidene-L-ascorbic Acid (Cyc-AA To a suspension of L-ascorbic acid (10.0 g, 56.8 mmol) in 100 mL acetone was added 1,1-dimethoxycyclohexane (13.9 g, 96.6 mmol) and 10-camphorsulfonic acid (0.66 g, 2.84 mmol). The resultant mixture was allowed to stir at room temperature under nitrogen atmosphere, and slowly became a clear, nearly colorless solution. After 48 hours, the solution had become pale yellow in color. Approximately 0.4 g of triethylamine was added, which resulted in the solution becoming nearly colorless again. The solvents were removed under reduced pressure to afford a white solid which was triturated with a 9:1 hexane/EtOAc mixture. The precipitate was collected via filtration and dried under vacuum to afford the product as a white solid (13.0 g, 89% yield). ¹H NMR signals were consistent with the desired product.

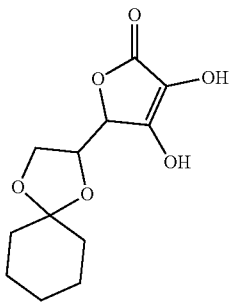 [SMILES: O=C1OC(C2COC3(CCCCC3)O2)C(O)=C1O]

Preparative Example 5 (PE-5): Synthesis of Nitrobenzyl-Protected Cyc-AA

Potassium carbonate (2.63 g, 19.0 mmol) was added to a solution of cyc-AA (4.87 g, 19.0 mmol) in 50 ml of 1:1 THF/DMSO. The resultant mixture was allowed to stir for 30 min. A solution of 2-nitrobenzyl bromide (4.11 g, 19.0 mmol) in 40 mL of 1:1 THF/DMSO was then added dropwise via addition funnel over 45 min. The resultant mixture was allowed to stir under nitrogen atmosphere overnight, during which time it became dark orange in color. Approximately 200 mL of H₂O was added to the mixture, which was then extracted with EtOAc (3×). The combined organic layers were washed with sat. aq. NaCl, dried over MgSO₄, filtered, and concentrated to an orange oil. This material was purified via suction filter chromatography (SiO₂, ramp eluent from 4:1 to 2:1 hexane/EtOAc) to afford 4.21 g of product as a yellow oil which foams under vacuum (57% yield). ¹H NMR was consistent with the desired product.

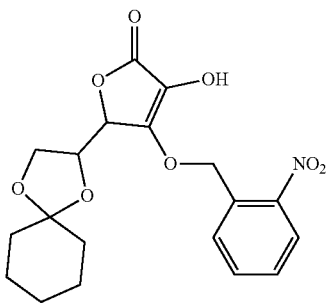 [SMILES: O=C1OC(C2COC3(CCCCC3)O2)C(OCc2ccccc2[N+](=O)[O-])=C1O]

Preparative Example 6 (PE-6): Synthesis of Nitrobenzyl Ascorbic Acid Palmitate (NBAscPalm)

Potassium carbonate (1.38 g, 10.0 mmol) was added to a solution of ascorbyl palmitate (4.15 g, 10.0 mmol) in 40 ml of 1:1 THF/DMSO. The resultant mixture was allowed to stir for 30 min. A solution of 2-nitrobenzyl bromide in 20 mL of 1:1 THF/DMSO was then added dropwise via addition funnel over 10 min. The resultant mixture was allowed to stir under nitrogen atmosphere for 70 hours, during which time it became dark orange in color. Approximately 200 mL of H₂O was added to the mixture, which was then extracted with EtOAc (3×). The combined organic layers were washed with brine, dried over MgSO₄, filtered, and concentrated to an orange oil. This material was purified via suction filter chromatography (SiO₂, ramp eluent from 5:1 to 3:1 hexane/EtOAc) to afford 2.27 g of product as a light tan solid (41% yield). ¹H NMR was consistent with the desired product.

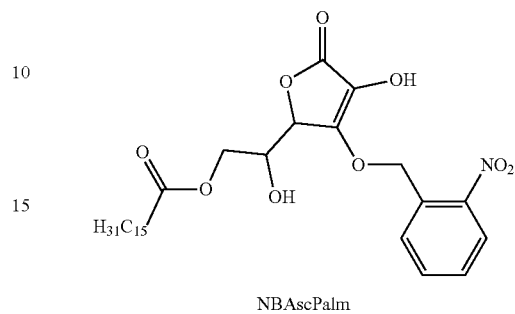

NBAscPalm

Preparative Example 7 (PE-7): Synthesis of Bis-Nitrobenzyl Ascorbic Acid Palmitate (NB₂AscPalm)

An oven-dried, 250-mL RB flask was cooled under nitrogen. The flask was charged with a stir bar, L-ascorbic acid-6-palmitate (9.53 g, 23.0 mmol), and the potassium carbonate (3.18 g, 23.0 mmol). The flask was then purged with nitrogen, after which time 60 mL THF and 60 mL DMSO were added. The mixture was stirred for 10 minutes at room temperature under nitrogen. The flask was purged again with nitrogen, after which time 2-nitrobenzyl bromide (4.97 g, 23.0 mmol) was added. This mixture was purged with nitrogen for 10 minutes, and allowed to stir at room temperature under nitrogen (flask wrapped in foil) for 5 days. Next, 120 mL sat. aq. NaCl was added to the mixture, followed by 100 mL ethyl acetate. The resulting mixture was shaken and separated, and the aqueous layer extracted with two further portions of 120 mL ethyl acetate. The resulting organic layer was washed with 3×150 mL water, dried over MgSO₄, filtered, and concentrated under reduced pressure to a red oil. This oil, when cooled, solidified into a dark red/brown solid that did not liquefy upon returning to room temperature. ¹H NMR of this crude material in d₆-DMSO showed there to be some impurities. Trituration of the crude material in hexanes followed by filtering appeared to remove some palmitic acid and leave behind a purer but still not clean material. Thin layer chromatography showed the primary product (RF=0.16) with a less-polar impurity (RF=0.50) in a 2:1 hexanes/EtOAc medium. These conditions were used to formulate a method on a BIOTAGE ISOLERA ONE automatic chromatography machine (Biotage USA, Charlotte, N.C.). Biotage columns were run on the crude material. Isolation of the RF=0.50 fraction showed it to be the diprotected product (NB₂AscPalm). The isolated yield of the diprotected product was 0.520 g (3% yield). Isolation of the RF=0.16 fraction showed it to be the monoprotected product shown above (PE-6). The isolated yield of the monoprotected product (NBAscPalm, PE-6) was 2.79 g (22% yield).

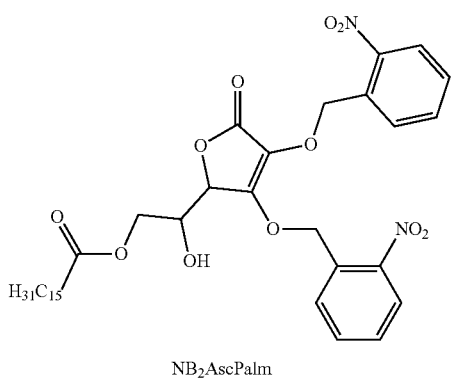

NB2AscPalm

Preparative Example 8 (PE-8): Synthesis of
Dimethoxy Nitrobenzyl Ascorbic Acid Palmitate Step 1: A solution of phosphorous tribromide (27.1 g, 100.0 mmol) in THF (100 mL) was added dropwise via addition funnel under nitrogen atmosphere to a stirring solution of 4,5-dimethoxy-2-nitrobenzyl alcohol (10.7 g, 50.0 mmol) in THF (200 mL). After stirring overnight, the THF was removed under reduced pressure, and the residue was partitioned between sat. aq. NaHCO$_3$ and EtOAc. The organic layer was then washed with sat. aq. NaCl, dried over MgSO$_4$, filtered, and concentrated to a dark yellow oil. This material was purified via suction filter chromatography (SiO$_2$, ramp eluent from 4:1 to 3:1 hexane/EtOAc). The product fractions were concentrated to afford 11.8 g of 1-(bromomethyl)-4,5-dimethoxy-2-nitrobenzene as a bright yellow solid (86% yield).

Step 2: Potassium carbonate (1.38 g, 10.0 mmol) was added to a solution of L-ascorbic acid-6-palmitate (4.15 g, 10.0 mmol) in 40 ml of 1:1 THF/DMSO. The resultant mixture was allowed to stir for 30 min. A solution of 1-(bromomethyl)-4,5-dimethoxy-2-nitrobenzene (2.76 g, 10.0 mmol) in 40 mL of 1:1 THF/DMSO was then added dropwise via addition funnel over 30 min. The resultant mixture was allowed to stir under nitrogen atmosphere overnight, during which time it became dark orange in color. Approximately 200 mL of H$_2$O was added to the mixture, which was then extracted with EtOAc (3×). The combined organic layers were washed with H$_2$O (2×) and sat. aq. NaCl, dried over MgSO$_4$, filtered, and concentrated to an orange oil. This material was purified via suction filter chromatography (SiO$_2$, ramp eluent from 4:1 to 3:1 hexane/EtOAc) to afford 2.44 g of product as a yellow oil which foams under vacuum (40% yield). $^1$H NMR was consistent with the desired product.

Preparative Example 9 (PE-9): Synthesis of
Dimethoxy Nitrobenzyl D-AA

Potassium carbonate (2.07 g, 15.0 mmol) was added to a solution of p-AA (3.24 g, 15.0 mmol) in 50 ml of 1:1 THF/DMSO. The resultant mixture was allowed to stir for 30 min. A solution of 1-(bromomethyl)-4,5-dimethoxy-2-nitrobenzene (prepared as in PE-8; 4.14 g, 15.0 mmol) in 50 mL of 1:1 THF/DMSO was then added dropwise via addition funnel over 10 min. The resultant mixture was allowed to stir under nitrogen atmosphere overnight, during which time it became dark orange in color. Approximately 200 mL of H$_2$O was added to the mixture, which was then extracted with EtOAc (3×). The combined organic layers were washed with sat. aq. NaCl, dried over MgSO$_4$, filtered, and concentrated to an orange oil. This material was purified via suction filter chromatography (SiO$_2$, ramp eluent from 2:1 to 1:1 hexane/EtOAc) to afford 3.50 g of product as a yellow oil which foams under vacuum (57% yield). $^1$H NMR was consistent with the desired product.

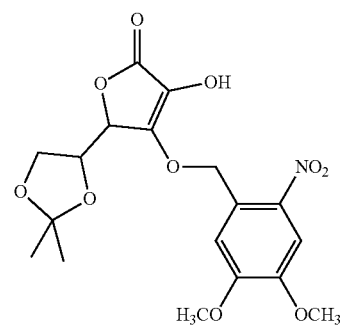

Preparative Example 10 (PE-10): Synthesis of
Dimethoxy Nitrobenzyl Ascorbic Acid The isopropylidene protected ascorbate PE-9 (3.50 g, 8.51 mmol) was dissolved in 80 mL of 1:1 THF/1N aq. HCl, and the resultant mixture was allowed to stir at room temperature overnight. A yellow precipitate which had formed was then removed via filtration, washing with additional H$_2$O. The filtrate was then extracted with EtOAc (3×), and the combined organic layers were washed with sat. aq. NaCl, dried over MgSO$_4$, filtered, and concentrated to afford 2.50 g of product as a yellow oil which foams under vacuum (79% yield). $^1$H NMR was consistent with the desired product.

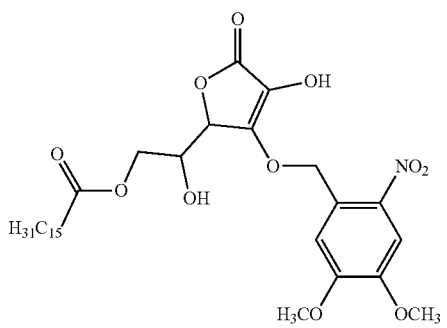

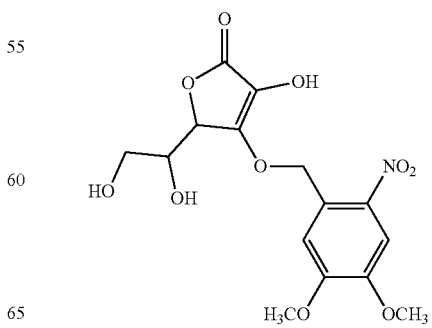

Preparative Example 11 (PE-11): Synthesis of Piperidinyl Nitrobenzyl p-AA

Step 1: (The 5-(piperidin-1-yl)-2-nitrobenzyl alcohol was prepared as in Org. Lett. 2007, 9, 5453.) A solution of phosphorous tribromide (4.58 g, 16.9 mmol) in THF (20 mL) was added dropwise via addition funnel under nitrogen atmosphere to a stirring solution of 5-(piperidin-1-yl)-2-nitrobenzyl alcohol (2.00 g, 8.46 mmol) in THF (30 mL). After stirring overnight, the THF was removed under reduced pressure, and the residue was partitioned between sat. aq. NaHCO$_3$ and EtOAc. The organic layer was then washed with sat. aq. NaCl, dried over MgSO$_4$, filtered, and concentrated to a dark yellow oil. This material was purified via suction filter chromatography (SiO$_2$, 4:1 hexane/EtOAc eluent). The product fractions were concentrated to afford 2.10 g of 5-(piperidin-1-yl)-2-nitrobenzyl bromide as a yellow oil which was used immediately in the subsequent step.

Step 2: Potassium carbonate (0.97 g, 7.02 mmol) was added to a solution of p-AA (1.52 g, 7.02 mmol) in 30 ml of 1:1 THF/DMSO. The resultant mixture was allowed to stir for 30 min. A solution of 5-(piperidin-1-yl)-2-nitrobenzyl bromide in 20 mL of 1:1 THF/DMSO was then added dropwise via addition funnel over 10 min. The resultant mixture was allowed to stir under nitrogen atmosphere overnight, during which time it became dark orange in color. Approximately 200 mL of H$_2$O was added to the mixture, which was then extracted with EtOAc (3×). The combined organic layers were washed with sat. aq. NaCl, dried over MgSO$_4$, filtered, and concentrated to an orange oil. This material was purified via suction filter chromatography (SiO$_2$, ramp eluent from 2:1 to 3:2 hexane/EtOAc) to afford 1.85 g of product as an orange oil which foams under vacuum (61% yield). $^1$H NMR was consistent with the desired product.

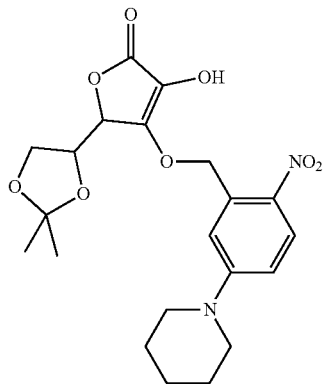 [SMILES: CC1(C)OCC(C2OC(=O)C(O)=C2OCc2cc(N3CCCCC3)ccc2[N+](=O)[O-])O1]

Preparative Example 12 (PE-12): Synthesis of Piperidinyl Nitrobenzyl Ascorbic Acid The isopropylidene protected ascorbate PE-11 (1.85 g, 4.26 mmol) was dissolved in 40 mL of 1:1 THF/1N aq. HCl, and the resultant mixture was allowed to stir at room temperature overnight. The THF was removed under reduced pressure, and the remaining aqueous layer was extracted with EtOAc (3×). The combined organic layers were then washed with sat. aq. NaCl, dried over MgSO$_4$, filtered, and concentrated to afford an orange oil. This material was purified via suction filter chromatography (SiO$_2$, ramp eluent from 1:1 to 1:4 hexane/EtOAc) to provide 1.20 g product as an orange solid (71% yield). $^1$H NMR was consistent with the desired product.

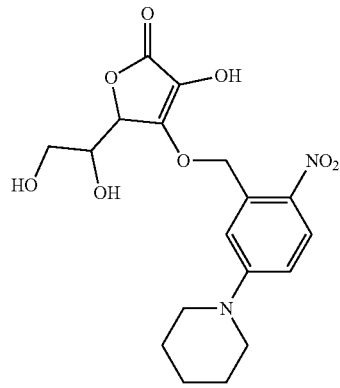 [SMILES: O=C1OC(C(O)CO)C(OCc2cc(N3CCCCC3)ccc2[N+](=O)[O-])=C1O]

Preparative Example 13 (PE-13): Synthesis of Coumarin-Protected p-AA

Step 1: In a 200 mL round-bottomed flask equipped with magnetic stirbar, 3-methoxyphenol (3.72 g, 30.0 mmol) and ethyl-4-chloroacetoacetate (7.41 g, 45.0 mmol) were added to methanesulfonic acid (40 mL), and the resultant mixture was allowed to stir at room temperature overnight. The mixture was then poured onto crushed ice, and the resultant precipitate was collected via vacuum filtration, washing with additional H$_2$O. This material was then dried under vacuum to afford an essentially quantitative yield of 4-chloromethyl-7-methoxycoumarin as a beige solid.

Step 2: In a 100 mL round-bottomed flask equipped with magnetic stirbar, 4-chloromethyl-7-methoxycoumarin (0.45 g, 2.00 mmol) was dissolved in acetone (20 mL). Potassium iodide (1.00 g, 6.02 mmol) was added, and the resultant mixture was heated to reflux overnight. The acetone was removed under reduced pressure, and the residue was partitioned between H$_2$O and EtOAc. The organic layer was washed with sat. aq. NaCl, dried over MgSO$_4$, filtered, and concentrated under reduced pressure to afford 0.62 g of 4-iodomethyl-7-methoxycoumarin as a yellow-orange solid (98% yield).

Step 3: Potassium carbonate (0.55 g, 4.00 mmol) was added to a solution of p-AA (0.86 g, 4.00 mmol) in 40 ml of 1:1 THF/DMSO. The resultant mixture was allowed to stir for 30 min. A solution of 4-iodomethyl-7-methoxycoumarin (0.62 g, 2.00 mmol) in 40 mL of 1:1 THF/DMSO was then added dropwise via addition funnel over 30 min. The resultant mixture was allowed to stir under nitrogen atmosphere overnight, during which time it became orange in color. The THF was removed under reduced pressure, and approximately 200 mL of H$_2$O was added to the residue, which was then extracted with EtOAc (3×). The combined organic layers were washed with sat. aq. NaCl, dried over MgSO$_4$, filtered, and concentrated to an orange oil. This material was purified via suction filter chromatography (SiO$_2$, EtOAc eluent) to afford 0.34 g of product as a yellow oil which foams under vacuum (43% yield). $^1$H NMR was consistent with the desired product.

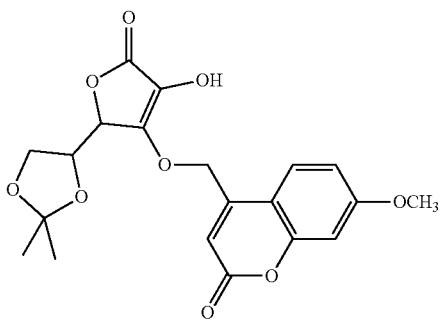 [SMILES: COc1ccc2c(COC3=C(O)C(=O)OC3C3COC(C)(C)O3)cc(=O)oc2c1]

Preparative Example 14 (PE-14): Synthesis of Dimethoxy Coumarin-Protected p-AA Potassium carbonate (38 mg, 0.28 mmol) was added to a solution of p-AA (61 mg, 0.28 mmol) in 1 ml of 1:1 THF/DMSO. A solution of 4-bromomethyl-6,7-dimethoxy-coumarin (84 mg, 0.28 mmol) in 1 mL of DMSO was then added dropwise via syringe. The resultant mixture was allowed to stir under nitrogen atmosphere overnight. The reaction mixture was then quenched via addition of 2 mL of $H_2O$, and the product was then extracted with EtOAc (3×). The combined organic layers were dried over $Na_2SO_4$, filtered, and concentrated under reduced pressure. The crude product was purified using a Biotage Isolera Flash Column Chromatography system with an eluent gradient of 50% to 80% EtOAc in hexanes, providing the product as a white solid (55 mg, 45% yield). $^1$H NMR was consistent with the desired product.

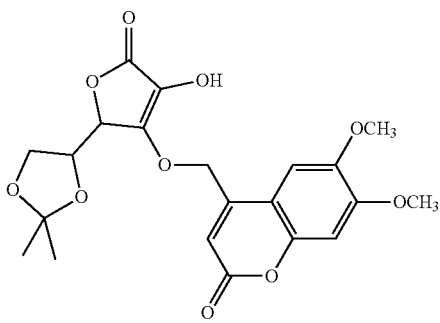 [SMILES: COc1cc2oc(=O)cc(COC3=C(O)C(=O)OC3C3COC(C)(C)O3)c2cc1OC]

Example 1 (EX-1): Two-Part Formulation Using the PE-2 Ascorbate

A representative two-part dental composite formulation was prepared as follows. A "Mixture-A" paste included a 1:1 mixture of BisGMA and TEGDMA as polymerizable methacrylate-based monomers, PE-2 as an ascorbate initiator, HDK H-2000 fumed silica as a flow agent, and Z250 as filler material, according to the amounts listed in Table 1. A "Mixture-B" paste included a 1:1 mixture of BisGMA and TEGDMA, a 1.7 wt % solution of $Cu(OAc)_2$ dissolved in 1:1 BisGMA/TEGDMA, cumene hydroperoxide (CHP), HDK H-2000 fumed silica, and Z250 filler, according to the amounts listed in Table 1.

TABLE 1

| | Mixture-A | | | Mixture-B | |
|---|---|---|---|---|---|
| Material | Wt. % | mass (g) | Material | Wt. % | mass (g) |
| BisGMA | 20.00 | 2.00 | BisGMA | 18.30 | 1.83 |
| TEGDMA | 20.00 | 2.00 | TEGDMA | 18.30 | 1.83 |
| — | — | — | $Cu(OAc)_2$ soln* | 1.40 | 0.14 |
| PE-2 | 0.60 | 0.06 | CHP | 1.00 | 0.10 |
| HDK H-2000 | 1.00 | 0.10 | HDK H-2000 | 2.00 | 0.20 |
| Z250 filler | 58.40 | 5.84 | Z250 filler | 59.00 | 5.90 |
| Total | 100.00 | 10.00 | Total | 100.00 | 10.00 |

*The "$Cu(OAc)_2$ soln" of EX-1 was prepared as a 1.7 wt. % solution of $Cu(OAc)_2$ in 1:1 BisGMA/TEGDMA; thus the Mixture-B paste was 0.024 wt. % $Cu(OAc)_2$ To perform curing experiments with the EX-1 two-part formulation, 60 mg portions of each of the Mixture-A and Mixture-B parts of EX-1 were weighed out onto a mixing pad and hand mixed together for 20 seconds. At time=30 seconds, the mixture was irradiated at 385 nm with an LX-400 LED lamp (Lumen Dynamics, Mississauga, Ontario, Canada) held 1.5 cm from the mixture for the specified time, as summarized in Table 2. A dental probe was then used to evaluate the cure of the material. Working time was defined as the elapsed time until the first solid chunk of cured material could be detected, and full cure was defined as the elapsed time until the entire sample had cured to a solid. Results were as summarized in Table 2.

TABLE 2*

| Irradiation time, seconds | 385 nm | |
|---|---|---|
| | work time, minutes | full cure, minutes |
| 0 | >480 | >480 |
| 1.0 | 1.50 | >480 |
| 2.0 | 0.83 | 3.00 |
| 3.0 | 0.67 | 1.75 |
| 5.0 | 0.33 | 1.00 |
| 10.0 | <0.17 | 1.00 |

*Work time = time until the first amount of cured material could be detected; Full cure = time until the entire paste sample became hardened.

Example 2 (EX-2): Two-Part Formulation Using the PE-3 Ascorbate

A two-part formulation was prepared according to the method described in Example 1, except that the PE-3 ascorbate initiator was used in place of the PE-2 ascorbate initiator, and using the amounts as summarized in Table 3.

TABLE 3

| | Mixture-A | | | Mixture-B | |
|---|---|---|---|---|---|
| Material | Wt. % | mass (g) | Material | Wt. % | mass (g) |
| BisGMA | 20.04 | 2.004 | BisGMA | 18.30 | 1.83 |
| TEGDMA | 20.03 | 2.003 | TEGDMA | 18.30 | 1.83 |
| — | — | — | $Cu(OAc)_2$ soln* | 1.40 | 0.14 |
| PE-3 | 0.53 | 0.053 | CHP | 1.00 | 0.10 |
| HDK H-2000 | 1.00 | 0.100 | HDK H-2000 | 2.00 | 0.20 |
| Z250 filler | 58.40 | 5.840 | Z250 filler | 59.00 | 5.90 |
| Total | 100.00 | 10.000 | Total | 100.00 | 10.00 |

*The "$Cu(OAc)_2$ soln" of EX-2 was prepared as a 1.7 wt. % solution of $Cu(OAc)_2$ in 1:1 BisGMA/TEGDMA; thus the Mixture-B paste was 0.024 wt. % $Cu(OAc)_2$

Example 3 (EX-3): Two-Part Formulation Using the PE-6 Ascorbate

A two-part formulation was prepared according to the method described in Example 1, except that the PE-6 ascorbate initiator was used in place of the PE-2 ascorbate initiator, and using the amounts as summarized in Table 4.

TABLE 4

| | Mixture-A | | | Mixture-B | |
|---|---|---|---|---|---|
| Material | Wt. % | mass (g) | Material | Wt. % | mass (g) |
| BisGMA | 19.83 | 1.983 | BisGMA | 18.30 | 1.83 |
| TEGDMA | 19.83 | 1.983 | TEGDMA | 18.30 | 1.83 |
| — | — | — | Cu(OAc)$_2$ soln* | 1.40 | 0.14 |
| PE-6 | 0.94 | 0.053 | CHP | 1.00 | 0.10 |
| HDK H-2000 | 1.00 | 0.100 | HDK H-2000 | 2.00 | 0.20 |
| Z250 filler | 58.40 | 5.840 | Z250 filler | 59.00 | 5.90 |
| Total | 100.00 | 10.000 | Total | 100.00 | 10.00 |

*The "Cu(OAc)$_2$ soln" of EX-3 was prepared as a 1.7 wt. % solution of Cu(OAc)$_2$ in 1:1 BisGMA/TEGDMA; thus the Mixture-B paste was 0.024 wt. % Cu(OAc)$_2$

Comparative Example 1 (CE-1): Two-Part Formulation Using D-AA

A comparative example of a two-part formulation was prepared according to the method used for Example 1, except that p-AA (PE-1) was used as the ascorbate initiator in place of the PE-2 ascorbate initiator, with amounts as summarized in Table 5.

TABLE 5

| | Mixture-A | | | Mixture-B | |
|---|---|---|---|---|---|
| Material | Wt. % | mass (g) | Material | Wt. % | mass (g) |
| BisGMA | 20.12 | 2.012 | BisGMA | 18.30 | 1.83 |
| TEGDMA | 20.11 | 2.011 | TEGDMA | 18.30 | 1.83 |
| — | — | — | Cu(OAc)$_2$ soln* | 1.40 | 0.14 |
| p-AA | 0.37 | 0.037 | CHP | 1.00 | 0.10 |
| HDK H-2000 | 1.00 | 0.100 | HDK H-2000 | 2.00 | 0.20 |
| Z250 filler | 58.40 | 5.840 | Z250 filler | 59.00 | 5.90 |
| Total | 100.00 | 10.000 | Total | 100.00 | 10.00 |

*The "Cu(OAc)$_2$ soln" of CE-1 was prepared as a 1.7 wt. % solution of Cu(OAc)$_2$ in 1:1 BisGMA/TEGDMA; thus the Mixture-B paste was 0.024 wt. % Cu(OAc)$_2$ To perform curing experiments with the EX-1, EX-2, EX-3, and CE-1 two-part formulation, 60 mg portions of each of the Mixture-A and Mixture-B parts of each example were weighed out onto a mixing pad and hand mixed together for 20 seconds. At time=30 seconds, the mixture was irradiated at 385 nm with an LX-400 LED lamp (Lumen Dynamics, Mississauga, Ontario, Canada) held 1.5 cm from the mixture for the specified time, as summarized in Table 6. A dental probe was then used to evaluate the cure of the material. Working time was defined as the elapsed time until the first solid chunk of cured material could be detected, and full cure was defined as the elapsed time until the entire sample had cured to a solid. Results were as summarized in Table 6.

TABLE 6*

| Two-part formulation | Irradiation (3 seconds at 385 nm) | Work time, minutes | Full cure, minutes |
|---|---|---|---|
| CE-1 | No | 0.50 | 1.00 |
| EX-1 | No | >480 | >480 |
| | Yes | 0.67 | 1.75 |
| EX-2 | No | >480 | >480 |
| | Yes | 0.75 | 3.00 |
| Ex-3 | No | >480 | >480 |
| | Yes | 1.08 | 9.00 |

*Work time = time until the first amount of cured material could be detected;
Full cure = time until the entire paste sample became hardened.

Example 4 (EX-4): Two-Part Formulation Using the PE-14 Coumarin-Protected Ascorbate A two-part formulation was prepared according to the method described in Example 1, except that the PE-14 ascorbate material was used in place of the PE-2 ascorbate material, and using the amounts as summarized in Table 7.

TABLE 7

| | Mixture-A | | | Mixture-B | |
|---|---|---|---|---|---|
| Material | Wt. % | mass (g) | Material | Wt. % | mass (g) |
| BisGMA | 19.90 | 0.995 | BisGMA | 18.95 | 1.895 |
| TEGDMA | 19.90 | 0.995 | TEGDMA | 18.95 | 1.895 |
| — | — | — | Cu(OAc)$_2$ soln* | 0.10 | 0.01 |
| PE-17 | 0.80 | 0.040 | CHP | 1.00 | 0.10 |
| HDK H-2000 | 1.00 | 0.050 | HDK H-2000 | 2.00 | 0.20 |
| Z250 filler | 58.40 | 2.920 | Z250 filler | 59.00 | 5.90 |
| Total | 100.00 | 5.000 | Total | 100.00 | 10.00 |

*The "Cu(OAc)$_2$ soln" of EX-4 was prepared as a 1.7 wt. % solution of Cu(OAc)$_2$ in 1:1 BisGMA/TEGDMA; thus the Mixture-B paste was 0.002 wt. % Cu(OAc)$_2$

Comparative Example 2 (CE-2): Two-Part Formulation Using D-AA

A comparative example of a two-part formulation was prepared according to the method used for Example 1, except that p-AA (PE-1) was used as the ascorbate initiator in place of the PE-2 ascorbate initiator, with amounts as summarized in Table 8.

TABLE 8

| | Mixture-A | | | Mixture-B | |
|---|---|---|---|---|---|
| Material | Wt. % | mass (g) | Material | Wt. % | mass (g) |
| BisGMA | 20.1 | 1.005 | BisGMA | 18.95 | 1.895 |
| TEGDMA | 20.1 | 1.005 | TEGDMA | 18.95 | 1.895 |
| — | — | — | Cu(OAc)$_2$ soln* | 0.10 | 0.010 |
| p-AA | 0.4 | 0.020 | CHP | 1.00 | 0.10 |
| HDK H-2000 | 1.0 | 0.050 | HDK H-2000 | 2.00 | 0.20 |
| Z250 filler | 58.4 | 2.920 | Z250 filler | 59.00 | 5.90 |
| Total | 100.0 | 5.000 | Total | 100.00 | 10.00 |

*The "Cu(OAc)$_2$ soln" of CE-2 was prepared as a 1.7 wt. % solution of Cu(OAc)$_2$ in 1:1 BisGMA/TEGDMA; thus the Mixture-B paste was 0.002 wt. % Cu(OAc)$_2$ To perform curing experiments with the EX-4 and CE-2 two-part formulation, 60 mg portions of each of the Mixture-A and Mixture-B parts of each example were weighed out onto a mixing pad and hand mixed together for 20 seconds. At time=30 seconds, the mixture was irradiated at the specified wavelength with an LX-400 LED lamp (Lumen Dynamics, Mississauga, Ontario, Canada) held 1.5 cm from the mixture for the specified time, as summarized in Table 9. A dental probe was then used to evaluate the cure of the material. Full cure was defined as the elapsed time until the entire sample had cured to a solid. Results were as summarized in Table 9.

TABLE 9*

| Two-part formulation | Irradiation (wavelength, time) | Full cure, minutes |
|---|---|---|
| CE-2 | None | 1.00 |
| EX-4 | None | >480 |
|  | 365 nm, 5 seconds | <0.60 |
| EX-4 | None | >480 |
|  | 385 nm, 5 seconds | <0.60 |
| Ex-4 | None | >480 |
|  | 400 nm, 5 seconds | <0.60 |

*Full cure = time until the entire paste sample became hardened.

Example 5 (EX-5): Two-Part Structural Adhesive Formulation Using the PE-2 Ascorbate Representative two-part structural adhesive formulations were prepared as follows. "Mixture-A" resins included 2-hydroxyethyl methacrylate (HEMA) as the polymerizable methacrylate-based monomer, an ammonium chloride solution consisting of 5 wt % benzyltributyl ammonium chloride dissolved in HEMA, and a copper (II) acetate solution, consisting of 1.7 wt % copper (II) acetate dissolved in HEMA, according to the amounts listed in Table 10. "Mixture-B" pastes included BENZOFLEX 9-88, CAB-O-SIL TS fumed silica as filler, an ascorbate initiator (either p-AA or PE-2), and cumene hydroperoxide (CHP), according to the amounts listed in Table 11.

TABLE 10

|  | Mixture-A1 | | Mixture-A2 | | Mixture-A3 | |
|---|---|---|---|---|---|---|
| Material | Wt % | Mass (g) | Wt % | Mass (g) | Wt % | Mass (g) |
| HEMA | 98.1 | 19.62 | 96.9 | 19.38 | 94.5 | 18.90 |
| Am. Cl soln* | 1.2 | 0.24 | 2.4 | 0.48 | 4.8 | 0.96 |
| Cu(OAc)$_2$ soln** | 0.7 | 0.14 | 0.7 | 0.14 | 0.7 | 0.14 |
| Total | 100.0 | 20.00 | 100.0 | 20.00 | 100.0 | 20.00 |

*The "Am. Cl. soln" was 20 wt. % benzyltributyl ammonium chloride in HEMA.
**The "Cu(OAc)$_2$ soln" of EX-5 was prepared as a 1.7 wt. % solution of copper (II) acetate in HEMA; thus the Mixture-A1, Mixture-A2, and Mixture-A3 resins were 0.012 wt. % copper (II) acetate.

TABLE 11

|  | Mixture-B1 | | Mixture-B2 | |
|---|---|---|---|---|
| Material | Wt % | Mass (g) | Wt % | Mass (g) |
| Benzoflex 9-88 | 89.3 | 2.68 | 85.0 | 2.55 |
| CAB-O-SIL TS720 | 1.7 | 0.05 | 1.7 | 0.05 |
| p-AA | 7.3 | 0.22 | — | — |

TABLE 11-continued

|  | Mixture-B1 | | Mixture-B2 | |
|---|---|---|---|---|
| Material | Wt % | Mass (g) | Wt % | Mass (g) |
| PE-2 | — | — | 11.6 | 0.35 |
| CHP | 1.7 | 0.05 | 1.7 | 0.05 |
| Total | 100.0 | 3.00 | 100.0 | 3.00 |

To perform curing experiments with the EX-5 two-part formulation, 0.25 mL of Mixture-B1 or Mixture-B2 was added to 2.00 g of Mixture-A1, Mixture-A2, or Mixture-A3 in an 8-mL glass vial and shaken briefly to mix. The vial was then irradiated at 365 nm with an LX-400 LED lamp (Lumen Dynamics, Mississauga, Ontario, Canada) held within 1 cm of the glass vial for the specified time. Working time was defined as the point at which the material was fully solidified and no longer able to flow. Irradiation and working times were as summarized in Table 12.

TABLE 12*

| Two-part formulation | Irradiation (seconds at 365 nm) | Work time, minutes |
|---|---|---|
| Mixture-A1 + Mixture-B1 | 0 | 5.50 |
| Mixture-A2 + Mixture-B1 | 0 | 4.00 |
| Mixture-A3 + Mixture-B1 | 0 | 2.75 |
| Mixture-A1 + Mixture-B2 | 0 | >480 |
|  | 60 | 13.00 |
| Mixture-A2 + Mixture-B2 | 0 | >480 |
|  | 60 | 12.00 |
| Mixture-A3 + Mixture-B3 | 0 | >480 |
|  | 60 | 8.00 |

*Work time = time until the material was fully solidified and no longer able to flow Example 6 (EX-6): Preparation of Reactive Oligomer Formulations Step 1: A mixture consisting of 2-ethylhexyl acrylate (2EHA), n-butyl acrylate (BA), acrylamide (Acm), and hydroxypropyl acrylate (HPA) as polymerizable monomers was dissolved in methyl ethyl ketone (MEK) in a glass bottle according to the amounts listed in Table 13. Nitrogen was bubbled through this mixture for four minutes, and the bottle was then sealed and placed in a Laundrometer rotating water bath for 24 hours at 60° C. After 24 hours the sample was analyzed using GPC according to the "Determination of Molecular Weight Distribution" method described above, and determined to have $M_w$=151,000, with 34.8 hydroxyl groups per chain.

Step 2: 2-isocyanatoethyl methacrylate (IEM) in the amount listed in Table 13 was added to the oligomer/MEK solution in a glass jar. The sealed jar was heated for 24 hours at 60° C. while being rotated on a mechanical roller. The resultant oligomer ("Reactive oligomer A") was calculated to have 17 methacrylates per chain. The weight percentages in Table 13 are with respect to a total weight of 2EHA, BA, Acm, and HPA.

TABLE 13

Composition of reactive oligomer A in Example 6

| Material Name | 2EHA (g) | BA (g) | Acm (g) | HPA (g) | MEK (g) | IEM (g) added in Step 2 |
|---|---|---|---|---|---|---|
| Reactive oligomer A | 37.2 (60 wt. %) | 18.6 (30 wt. %) | 4.34 (7 wt. %) | 1.86 (3 wt. %) | 62.0 | 1.10 |

Formulations were then prepared by combining the Reactive oligomer A described above with ethoxylated bisphenol A dimethacrylate (SR348, obtained from Sartomer, Exton, Pa.), cumene hydroperoxide (CHP), copper (II) naphthenate (Cu(naph)$_2$), and either ascorbate PE-7 or PE-8, according to the amounts listed in Table 14. Each of the formulations was thoroughly mixed to ensure complete dissolution of the PE-7 or PE-8 ascorbate.

TABLE 14

Formulations for Example 6

| Formulation Name | Reactive oligomer A, 50 wt. % in MEK (g) | SR 348 (g) | CHP (g) | Cu(naph)$_2$ (g) | NBAscPalm (g) | NB$_2$AscPalm (g) |
|---|---|---|---|---|---|---|
| A2 | 20.0 | 1.0 | 0.025 | 0.032 | 0.023 | — |
| B2 | 20.0 | 2.0 | 0.025 | 0.032 | — | 0.028 |

Static shear experiments with the formulations in EX-6 were performed according to the "Static Shear Test Method" described above. Samples were either exposed to approximately 11 J/cm$^2$ of UVA according to an EIT POWERPUCK II (EIT, Sterling, Va.), or not exposed to a UV source. The resulting time to bond failure (in minutes) listed in Table 15 were means from triplicate measurements, with standard deviations (in minutes) listed in parentheses. Tests were discontinued after 10,000 minutes of hanging time, and the failure mode for each of the samples that failed was cohesive.

TABLE 15

| Formulation | Light exposure (~11 J/cm$^2$ of UVA) | Time to bond failure (min) |
|---|---|---|
| A2 | No | 10.7 (1.5) |
|  | Yes | >10000 |
| B2 | No | 3.0 (1.0) |
|  | Yes | >10000 |

Example 7 (EX-7): Preparation of Reactive Oligomer Formulations

A reactive oligomer-containing formulation was prepared according to the method described in Example 6, except that ethyl acetate (EtOAc) was used in place of the MEK, and using the amounts as summarized in Table 16. Note that the compositions of the two reactive oligomer samples are identical; the difference between them was only that reactive oligomer B had an M$_w$ of 300,000 (PDI 4.0) according to GPC, whereas the M$_w$ of reactive oligomer C was 283,000 (PDI 4.3). This difference was not considered significant. The amount of IEM added in Step 2 was calculated to give 9.3 methacrylates per chain in each case. For each reactive oligomer sample, 50 g MEK was added along with the IEM in Step 2, meaning that the final reactive oligomer solutions were 40 wt. % solids in EtOAc/MEK.

TABLE 16

Compositions of Reactive Oligomers B and C for Example 7

| Material Name | 2EHA (g) | BA (g) | Acm (g) | HPA (g) | EtOAc (g) | IEM (g) added in Step 2 |
|---|---|---|---|---|---|---|
| Reactive oligomer B | 62.0 | 30 | 5.0 | 3.0 | 100 | 0.480 |
| Reactive oligomer C | 62.0 | 30 | 5.0 | 3.0 | 100 | 0.510 |

Formulations were then prepared as in Example 6, according to the amounts listed in Table 17.

TABLE 17

Formulations for Example 7

| Formulation Name | Reactive oligomer B, 40 wt. % in EtOAc/MEK (g) | Reactive oligomer C, 40 wt. % in EtOAc/MEK (g) | SR 348 (g) | SR 350 (g) | CHP (g) | Cu(naph)$_2$ (g) | NBAscPalm (g) |
|---|---|---|---|---|---|---|---|
| A3 | 25.0 | — | 1.0 | — | 0.025 | 0.032 | 0.023 |
| B3 | 25.0 | — | 2.0 | — | 0.025 | 0.032 | 0.023 |
| C3 | 25.0 | — | — | 1.0 | 0.025 | 0.032 | 0.023 |
| D3 | 25.0 | — | — | 2.0 | 0.025 | 0.032 | 0.023 |
| E3 | — | 25.0 | — | 3.0 | 0.025 | 0.032 | 0.023 |
| F3 | — | 25.0 | — | 4.0 | 0.025 | 0.032 | 0.023 |

Overlap shear experiments with the formulations in EX-7 were performed according to the "Overlap Shear Test Method" described above. Samples were either exposed to approximately 2 J/cm$^2$ of UVA according to an EIT POWERPUCK II (EIT, Sterling, Va.), or not exposed to a UV source. The peak stress values and peak load values listed in Table 18 were means from triplicate measurements.

TABLE 18

| Formulation | Light exposure (~2 J/cm$^2$) | Peak stress, psi (kPa) | Peak load, lbf (Newton) | Failure mode |
|---|---|---|---|---|
| A3 | No | 44.6 (307) | 22.3 (99.2) | Cohesive |
|  | Yes | 28.0 (193) | 14.0 (62.3) | Cohesive |
| B3 | No | 53.8 (371) | 26.9 (120) | Cohesive |
|  | Yes | 13.1 (90.3) | 6.5 (29) | Cohesive |

TABLE 18-continued

| Formulation | Light exposure (~2 J/cm$^2$) | Peak stress, psi (kPa) | Peak load, lbf (Newton) | Failure mode |
|---|---|---|---|---|
| C3 | No | 175.9 (1212) | 87.9 (391) | Cohesive |
|  | Yes | 139.1 (959) | 69.6 (310) | Cohesive |
| D3 | No | 170.8 (1177) | 85.4 (380) | Cohesive |
|  | Yes | 303.5 (2092) | 151.7 (674.7) | Adhesive |
| E3 | No | 100.4 (692) | 50.2 (223) | Cohesive |
|  | Yes | 394.3 (2720) | 197.1 (876.7) | Adhesive |
| F3 | No | 25.2 (174) | 12.6 (56.0) | Cohesive |
|  | Yes | 440.3 (3035) | 220.2 (979.4) | Adhesive |

Example 8 (EX-8): Monitoring Cure by FTIR

Formulations were prepared as in Example 6, except that Reactive Oligomer B was used in place of Reactive Oligomer A, and using the amounts listed in Table 19.

TABLE 19

Formulations for Example 8

| Formulation Name | Reactive oligomer B, 40% in EtOAc/MEK (g) | SR 348 (g) | CHP (g) | Cu(naph)$_2$ (g) | NBAscPalm (g) | NB$_2$AscPalm (g) |
|---|---|---|---|---|---|---|
| A5 | 25.0 | 1.5 | 0.025 | 0.032 | 0.023 | — |
| B5 | 25.0 | 1.5 | 0.025 | 0.032 | — | 0.028 |

The above solutions were coated on T-10 release liner at 20 mil (~510 micrometers) thickness and subsequently dried in a 70° C. oven for 30 minutes (final film thickness ~5 mil (~127 micrometers)). The films were then folded over three times to reach a thickness of ~40 mil (~1000 micrometers). The general procedure "Cure Monitoring by FTIR" described above was then followed. Irradiation of the samples came in the form of passes through a Fusion Processor (a conveyor-belt UV system. LH10 FUSION PROCESSOR, Heraeus Noblelight America, Gaithersburg, Md.). The specifications were as follows: ~2 J/cm$^2$ UVA per pass as measured by EIT POWERPUCK II, 100% power on D-bulb.) At a time designated as "time zero", some samples were exposed for "1 pass" through the Fusion Processor, some for "2 passes", some for "4 passes", and some for "no passes" (i.e., no irradiation—these samples are designated as A5 and B5 in Table 20). Extent of cure was monitored using the area under the methacrylate peak in FTIR (6221-6100 cm$^{-1}$). At various time points after irradiation, the area under the peak was compared to the area before irradiation, and this comparison led to a % cure value (disappearance of methacrylates was equated to curing). The % cure results are shown below in Table 20.

TABLE 20

Curing Times for Formulations in Example 8

| A5, "no passes" | | B5, "no passes" | |
|---|---|---|---|
| Time after "time zero" (min) | % Cure | Time after "time zero" (min) | % Cure |
| 0 | 0.0 | 0 | 0.0 |
| 44 | 0.5 | 46 | 1.2 |
| 55 | 0.0 | 57 | 1.1 |
| 87 | 0.3 | 88 | 1.8 |
| 145 | 0.3 | 147 | 2.0 |
| 805 | 1.1 | 806 | 2.1 |
| 1446 | 0.8 | 1449 | 1.4 |
| 2922 | 1.1 | 2924 | 1.8 |
| 5676 | 1.4 | 5678 | 1.7 |
| 11501 | 1.2 | 11503 | 1.7 |
| 15421 | 3.0 | 15423 | 2.9 |
| 20019 | 3.3 | 20021 | 3.1 |
| 25939 | 4.5 | 25942 | 4.1 |
| 32733 | 4.5 | 32735 | 5.1 |
| 46073 | 4.5 | 46075 | 5.2 |

| A5, 1 Pass | | B5, 1 Pass | |
|---|---|---|---|
| Time after irradiation (min) | % Cure | Time after irradiation (min) | % Cure |
| 0 | 0.0 | 0 | 0.0 |
| 2 | 0.8 | 3 | 1.2 |
| 6 | 1.3 | 8 | 0.4 |
| 15 | 0.5 | 16 | 0.3 |
| 66 | 1.4 | 68 | 1.0 |
| 125 | 4.6 | 127 | 2.6 |
| 785 | 18.9 | 787 | 25.9 |
| 1427 | 18.8 | 1430 | 28.1 |
| 2902 | 19.2 | 2904 | 28.0 |

| A5, 2 Passes | | B5, 2 Passes | |
|---|---|---|---|
| Time after irradiation (min) | % Cure | Time after irradiation (min) | % Cure |
| 0 | 0.0 | 0 | 0.0 |
| 3 | 2.9 | 4 | 0.8 |
| 11 | 2.3 | 12 | 0.6 |
| 25 | 2.3 | 26 | 0.6 |
| 68 | 3.1 | 69 | 1.0 |
| 127 | 8.9 | 128 | 3.0 |
| 787 | 32.7 | 788 | 19.7 |
| 1430 | 32.4 | 1431 | 21.1 |
| 2904 | 32.7 | 2906 | 21.0 |

| A5, 4 Passes | | B5, 4 Passes | |
|---|---|---|---|
| Time after irradiation (min) | % Cure | Time after irradiation (min) | % Cure |
| 0 | 0.0 | 0 | 0.0 |
| 4 | 3.7 | 5 | 3.3 |
| 13 | 4.6 | 14 | 2.7 |
| 25 | 4.7 | 26 | 2.7 |
| 67 | 8.1 | 68 | 3.6 |
| 125 | 12.0 | 127 | 6.4 |
| 786 | 23.8 | 787 | 29.2 |
| 1429 | 23.4 | 1431 | 29.0 |
| 2903 | 24.1 | 2905 | 29.3 |

Example 9 (EX-9): Rheometric Monitoring of Cure in a Formulated Adhesive

A representative adhesive formulation was prepared according to the amounts listed in Table 21. The mixture consisted of butyl diglycol methacrylate (BDGMA), 2-hydroxyethyl methacrylate (HEMA), cyclohexyl methacrylate (CHMA), and ethoxylated bisphenol A dimethacrylate (SR348, obtained from Sartomer, Exton, Pa.) as polymerizable monomers, as well as BAYMOD 35.42 (BAYMOD), Sipomer PAM200 (PAM), ESS50F, HDK H18, DRAGONITE SW, and KRATON 1192.

TABLE 21

Formulations for Example 9

| Material | Wt. % | mass (g) |
|---|---|---|
| BDGMA | 28.95 | 39.42 |
| BAYMOD | 7.96 | 10.84 |
| HEMA | 15.26 | 20.79 |
| CHMA | 11.91 | 16.22 |
| PAM | 3.14 | 4.27 |
| ESS50F | 1.05 | 1.42 |
| HDK H18 | 1.05 | 1.42 |
| DRAGONITE | 17.57 | 23.92 |
| KRATON 1192 | 5.20 | 7.08 |
| SR348 | 7.93 | 10.80 |
| Total | 100.0 | 136.20 |

This formulation was then utilized in two-part adhesive formulations, prepared as shown in the representative example below. For each experiment, a "Mixture-A" consisted of propylene carbonate, tetrahydrofuran (THF), the PE-7 ascorbate, and cumene hydroperoxide (CHP), according to the amounts listed in Table 22. A "Mixture-B" consisted of the Formulation EX-9 and copper (II) naphthenate (Cu(naph)$_2$), according to the amounts listed in Table 22.

TABLE 22

| Mixture-A | | Mixture-B | |
|---|---|---|---|
| Material | Mass (g) | Material | Mass (g) |
| Propylene carbonate | 0.500 | Formulation from EX-9 | 10.000 |
| THF | 0.500 | Cu(naph)$_2$ | 0.050 |

TABLE 22-continued

| Mixture-A | | Mixture-B | |
|---|---|---|---|
| Material | Mass (g) | Material | Mass (g) |
| PE-7 | 0.075 | — | — |
| CHP | 0.075 | — | — |

To perform the curing experiments, the Mixture-A and Mixture-B were combined and hand-mixed. A portion of the resulting mixture was placed on a TA Instruments ARES G2 RHEOMETER (Waters Corporation, Milford, Mass.) and irradiated for the appropriate time period with stirring (S-2000 light source with 8 mm light guide, 100% power, ~1 inch (~2.5 cm) distance). The approximate intensity of the UV light applied in the experiments was 1540 mW/cm$^2$ in UVA, 10 mW/cm$^2$ in UVB, 760 mW/cm$^2$ in UVA2, and 1850 mW/cm$^2$ in UVV. Directly after irradiation, the rheometer plates were closed and the run began (25 mm parallel-plate geometry, isothermal oscillatory time sweep). Representative rheometry data values, including gel time and storage modulus (G', in Pa, kPa, or MPa), are shown in Table 23 below.

TABLE 23

| Sample | Irradiation time (seconds) | G' just after irradiation | Gel time (minutes) | G' after 2.5 h | G' after 7.5 h |
|---|---|---|---|---|---|
| Mixture-A + Mixture-B | 0 | 9.0 Pa | 257 | 15.0 Pa | 10 kPa |
| Mixture-A + Mixture-B | 15 | 30.0 Pa | 24 | 220 kPa | — |
| Mixture-A + Mixture-B | 20 | 50.0 Pa | 17 | 430 kPa | 2.2 MPa |
| Mixture-A + Mixture-B | 30 | 3.4 kPa | Gelled after UV | 340 kPa | — |

To perform overlap shear experiments with the formulations in EX-9, Mixture-A and Mixture-B samples were combined and thoroughly mixed. 1"×0.5"×0.064" (2.5 cm×1.3 cm×0.16 cm) aluminum coupons were prepared by abrading the terminal 1" (2.5 cm) with a SCOTCH-BRITE PAD (#7447) and wiping/washing the dust away with paper towels and isopropanol. The overlap shear samples were made as follows: six coupons were labeled and laid out in a 2×3 array such that their abraded ends abutted in the middle. A strip of 5-mil (~127 micrometers) thick vinyl tape was applied to either side of the abraded areas, 0.5" (1.3 cm) from the end of the coupons in each case. A portion of the mixed sample was applied to the top pair of coupons between the strips of tape. A glass slide was then used as a coating knife to spread a uniform, 5-mil (~127 micrometers) layer of adhesive over the desired bond areas, with the tape serving as the spacer. The coated samples were used to create 1"×0.5" (2.5 cm×1.3 cm) overlap bonds, either right away (in the case of the Control samples) or sent through the FUSION PROCESSOR (a conveyor-belt UV system; LH10 FUSION PROCESSOR, HERAEUS NOBLELIGHT AMERICA, Gaithersburg, Md.) at a given speed. If the samples were sent through the FUSION PROCESSOR, the overlap bonds were constructed shortly after irradiation (within 2 min). The Control samples did not go through the FUSION PROCESSOR at all. The 0.5 J samples went through (D Bulb) at 100 fpm (~30 meters per minute), giving an overall radiation exposure of 500 mJ/cm$^2$ UVA, 155 mJ/cm$^2$ UVB, 15 mJ/cm$^2$ UVC, and 550 mJ/cm$^2$ UVV, according to the EIT POWERPUCK II. The 1 J samples went through at 48 fpm (~15 meters per minute) and received double the exposure of the 0.5 J samples. The 2 J samples went through at 23 fpm (~7 meters per minute) and received quadruple the exposure of the 0.5 J samples. For each irradiation level (Control, 0.5 J, 1 J, 2 J), six specimens were made: three to be tested 4 hours after overlap bond construction, and three to be tested 24 hours after overlap bond construction. Thus there were 24 specimens in total, each labeled accordingly. Four hours after overlap bond construction, each of the specimens labeled "4 h" was tested on the MTS SINTECH TENSILE TESTER (MTS Systems Corporation, Eden Prairie, Minn.) with a 5000-lb (~2270 kg) load cell and a strain rate of 0.1 in/min (0.25 cm/min). 24 hours after overlap bond construction, each of the specimens labeled "24 h" was similarly tested. The peak stress values and peak load values listed in Table 24 were means from triplicate measurements.

TABLE 24

| Specimen | Time after overlap bond construction (hours) | Peak stress, psi (kPa) | Peak load, lbf (Newton) | Failure mode |
|---|---|---|---|---|
| Control | 4 | 40.0 (276) | 20.0 (89.0) | Cohesive |
| | 24 | 301.5 (2078) | 150.8 (670.7) | Cohesive |
| 0.5J | 4 | 650.7 (4486) | 325.3 (1447) | Cohesive |
| | 24 | 254.7 (1756) | 127.4 (566.7) | Cohesive |
| 1J | 4 | 625.9 (4315) | 312.9 (1391) | Cohesive |
| | 24 | 68.2 (470) | 34.1 (152) | Cohesive |
| 2J | 4 | 830.7 (5727) | 415.4 (1847) | Cohesive |
| | 24 | 100.4 (692.2) | 50.2 (223) | Cohesive |

Example 10 (EX-10): Nozzle Life Test for a Formulated Adhesive

A two-part adhesive formulation was prepared as shown in table 25 below. A "Mixture-A" paste consisted of propylene carbonate, tetrahydrofuran (THF), the PE-7 ascorbate cumene hydroperoxide (CHP), and H18 fumed silica (HDK H18, Wacker Chemical Corp., Adrian, Mich.) according to the amounts listed in Table 25. A "Mixture-B" consisted of the formulation from EX-9 and copper (II) naphthenate (Cu(naph)$_2$), according to the amounts listed in Table 25. Mixture-A was placed into the small side of a 10:1 cartridge, while Mixture-B was placed into the large side of the same cartridge. A static mixing nozzle with a 20 gauge needle was affixed to the cartridge. The back end of the cartridge was hooked up to an EFD ULTRA 1400 liquid dispensing controller. The pressure was set to 6 bar (600 kPa).

TABLE 25

| Mixture-A | | Mixture-B | |
|---|---|---|---|
| Material | Mass (g) | Material | Mass (g) |
| Propylene carbonate | 2.00 | Formulation EX-9 | 20.00 |
| THF | 2.00 | Cu(naph)$_2$ | 0.10 |
| PE-7 | 0.15 | — | — |
| CHP | 0.15 | — | — |
| H18 fumed silica | 1.20 | — | — |

To perform the nozzle life tests, the contents of the cartridge were extruded for 10 seconds at 6 bar (600 kPa), and the extruded material was weighed directly after. This was done at various time points. In between the time points, the mixed adhesive was allowed to sit in the needle. Just before each time point, a 1-second extrusion pulse was applied to clean the drop on the end of the needle. The data points for the amount of extruded adhesive are shown in Table 26, with duplicates for each time point. The extruded amounts remained almost the same throughout all time points, which signifies little to no clogging of the needle even at intervals of hours.

TABLE 26

| | Mass of extruded material (g) | |
|---|---|---|
| Time | Run 1 | Run 2 |
| Initial | 0.37 | 0.37 |
| 5 min | 0.35 | 0.35 |
| 15 min | 0.36 | 0.36 |
| 30 min | 0.34 | 0.34 |
| 1 h | 0.34 | 0.34 |
| 2 h | 0.33 | 0.34 |
| 6.5 h | 0.36 | 0.35 |

What is claimed is:

1. A polymerizable composition comprising a polymerizable component, and a redox initiation system comprising:
    a) a transition metal complex that participates in a redox cycle;
    b) an oxidizing agent
    c) a photolabile reducing agent of the formula:

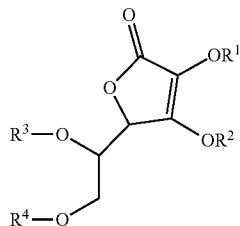

where
    each of $R^1$ and $R^2$ are H, an alkyl, an aryl, or $R^{Photo}$, with the proviso that at least one of $R^1$ and $R^2$ is $R^{Photo}$;
    $R^{Photo}$ is a photolabile group;
    each of $R^3$ and $R^4$ are independently H, an alkyl, an aryl comprising an ester, an ether, a urethane or a carbonate functional group.

2. The polymerizable composition of claim 1, wherein the photolabile group $R^{Photo}$ is selected from phenacyl groups, 2-alkylphenacyl groups, ethylene-bridged phenacyl groups, p-hydroxyphenacyl groups, benzoin groups, o- or p-nitrobenzyl groups, o-nitro-2-phenethyloxycarbonyl groups, coumarin-4-yl methyl groups, benzyl groups, o- or p-hydroxylbenzyl groups, o- or p-hydroxynaphthyl groups, 2,5-dihydroxyl benzyl groups, 9-phenylthioxanthyl, 9-phenylxanthyl groups, anthraquinon-2-yl groups, 8-halo-7-hydroxyquinoline-2-yl methyl groups, and pivaloylglycol groups.

3. The polymerizable composition of claim 1 wherein the transition metal complex is of the formula:
    $[ML_p]^{n+}A^-$, wherein M is a transition metal that participates in a redox cycle,
    L is a ligand, A– is an anion, n is the formal charge on the transition metal having a whole number value of 1 to 7, and p is the number of ligands on the transition metal having a number value of 1 to 9.

4. The polymerizable composition of claim 1 wherein the redox initiator system is present in the composition in amounts, from 0.1 to about 10 parts by weight, based on 100 parts by weight of the polymerizable component of the polymerizable composition.

5. The polymerizable composition of claim 1 wherein further comprising a secondary reducing agent selected from tertiary amines; aromatic sulfinic salts; thioureas; and mixtures thereof.

6. The polymerizable composition of claim 1 wherein the oxidizing agent of the redox initiator system is selected from persulfuric acid and salts thereof; peroxides, salts of transition metals, perboric acid and salts thereof, permanganic acid and salts thereof, perphosphoric acid and salts thereof, and mixtures thereof.

7. The polymerizable composition of claim 1 comprising one or more polymerizable vinyl monomers and the redox initiator system, wherein the vinyl monomer is selected from vinyl ethers, vinyl esters, styrenes, substituted styrene, vinyl halides, divinylbenzene, alkenes, isoprene, butadiene and mixtures thereof.

8. The polymerizable composition of claim 1 wherein the molar ratio of the transition metal complex relative to oxidizing agent is from 1:1000 to 1:5.

9. The polymerizable composition of claim 1 wherein the mole ratio of the oxidizing agent to the photolabile reducing agent is from 1:1.5 to 1.5:1.

10. The polymerizable composition of claim 1 further comprising 1-35 parts by weight of a toughening agent, relative to 100 parts by weight of the polymerizable component of the polymerizable composition.

11. The polymerizable composition of claim 1 wherein at least one of $R^3$ and $R^4$ comprises a $C_{12}$-$C_{20}$ alkyl group.

12. The polymerizable composition of claim 1 wherein the transition metal complex is Cu(II) naphthenate.

13. A method of polymerization of the polymerizable composition of claim 1 comprising combining a first mixture comprising the transition metal complex and a second mixture comprising the oxidizing agent and the photolabile reducing agent, a polymerizable component in the first and/or the second mixture, and irradiating the resulting combined mixture to photolyze the photolabile transition metal complex and initiate the redox polymerization cycle.

14. A multilayer article comprising a coating of the polymerizable composition of claim 1 on a substrate.

* * * * *